United States Patent
Pericas-Brondo et al.

(10) Patent No.: US 9,271,959 B2
(45) Date of Patent: Mar. 1, 2016

(54) BICYCLIC TETRAHYDROPYRROLE COMPOUNDS

(71) Applicant: Laboratorios del Dr. Esteve, S.A., Barcelona (ES)

(72) Inventors: Miguel Angel Pericas-Brondo, Esplugues de Llobregat (ES); Antonio Torrens-Jover, Terrassa (ES); Susana Yenes-Minguez, Molins de Rei (ES); Felix Cuevas Cordobes, Madrid (ES); Carmen Garcia Granda, Madrid (ES)

(73) Assignee: LABORATORIOS DEL DR. ESTEVE, S.A., Barcelona (ES)

( * ) Notice: Subject to any disclaimer, the term of this patent is extended or adjusted under 35 U.S.C. 154(b) by 538 days.

(21) Appl. No.: 13/661,965

(22) Filed: Oct. 26, 2012

(65) Prior Publication Data

US 2013/0072456 A1 Mar. 21, 2013

Related U.S. Application Data

(62) Division of application No. 12/226,559, filed as application No. PCT/EP2007/003827 on Apr. 30, 2007, now Pat. No. 8,372,990.

(30) Foreign Application Priority Data

Apr. 28, 2006 (EP) .................................. 06384010

(51) Int. Cl.
*A61K 31/403* (2006.01)
*C07D 209/52* (2006.01)
*C07D 209/94* (2006.01)

(52) U.S. Cl.
CPC ............ *A61K 31/403* (2013.01); *C07D 209/52* (2013.01); *C07D 209/94* (2013.01)

(58) Field of Classification Search
None
See application file for complete search history.

(56) References Cited

U.S. PATENT DOCUMENTS

2004/0044029 A1 * 3/2004 Dart et al. .................... 514/307

FOREIGN PATENT DOCUMENTS

| EP | 0648762 A2 | 4/1995 |
|----|------------|--------|
| WO | WO 2004/013117 A1 | 2/2004 |
| WO | WO 2007/061741 | * 5/2007 |

OTHER PUBLICATIONS

Su et al. In Current Medicinal Chemistry, 10(20), 2073-2080 (2003).*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Diaz et al. In Central Nervous System Agents in Medicinal Chemistry, 2009, 9, 172-183.*
International Search Report issued by the International Searching Authority (ISA/EP) on Aug. 22, 2007 in connection with International Application No. PCT/EP2007/003827.
Written Opinion of the International Searching Authority issued by the International Searching Authority (ISA/EP) on Aug. 22, 2007 in connection with International Application No. PCT/EP2007/003827.
Matsuno et al., In Behavioural Brain Research, 1997, 83:221-224.
J.G. Gannon, Chapter Nineteen in Burger's Medicinal Chemistry and Drug Discovery, Fifth Edition, vol. 1: Principles and Practice, Wiley-Interscience, 1995, 783-802, 784.
Schafer et al., Drug Discovery Today, 2008, 13 (21/22), 913-916.
Honig et al., Journal of Translational Medicine, 2004, 2(44).
Office Action issued Mar. 24, 2010 in connection with U.S. Appl. No. 12/226,559, filed Mar. 3, 2009.
Office Action issued Jul. 22, 2010 in connection with U.S. Appl. No. 12/226,559, filed Mar. 3, 2009.
Office Action issued Mar. 23, 2011 in connection with U.S. Appl. No. 12/226,559, filed Mar. 3, 2009.
Final Office Action issued Aug. 15, 2011 in connection with U.S. Appl. No. 12/226,559, filed Mar. 3, 2009.
Advisory Action issued Nov. 25, 2011 in connection with U.S. Appl. No. 12/226,559, filed Mar. 3, 2009.
Office Action issued Dec. 27, 2011 in connection with U.S. Appl. No. 12/226,559, filed Mar. 3, 2009.
Final Office Action issued Apr. 23, 2012 in connection with U.S. Appl. No. 12/226,559, filed Mar. 3, 2009.
Notice of Allowance issued Jul. 27, 2012 in connection with U.S. Appl. No. 12/226,559, filed Mar. 3, 2009.

* cited by examiner

*Primary Examiner* — Dennis Heyer
(74) *Attorney, Agent, or Firm* — John P. White; Cooper & Dunham LLP

(57) ABSTRACT

The present invention relates to substituted bicyclic tetrahydropyrrole compounds of general formula (I), methods for their preparation, medicaments comprising these compounds as well their use in the manufacture of a medicament for the treatment of humans and animals.

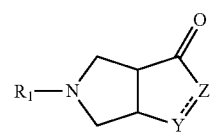

(I)

7 Claims, No Drawings

BICYCLIC TETRAHYDROPYRROLE COMPOUNDS

This application is a divisional of U.S. Ser. No. 12/226,559, filed Mar. 3, 2009, now allowed, §371 national stage of PCT International Application No. PCT/EP2007/003827, filed Apr. 30, 2007, which claims priority of European Patent Application No. 06384010.2, filed Apr. 28, 2006, the contents of all of which are hereby incorporated by reference into this application.

FIELD OF THE INVENTION

The present invention relates to compounds having pharmacological activity towards the sigma (σ) receptor, and more particularly to some bicyclic tetrahydropyrrole derivatives, to processes of preparation of such compounds, to medicaments comprising them, and to their use in therapy and prophylaxis, in particular for the treatment of Alzheimer's disease.

BACKGROUND OF THE INVENTION

Alzheimer's disease (AD) is a progressive, irreversible brain disorder with no known cause or cure. Symptoms of the disease include memory loss, confusion, impaired judgment, personality changes, disorientation, and loss of language skills. Always fatal, Alzheimer's disease is the most common form of irreversible dementia.

According to the American Health Assistance Foundation (AHAF), more than 4.5 million Americans are believed to have Alzheimer's disease and by 2050, the number could increase to 13.2 million. In every nation where life expectancy has increased, so has the incidence of Alzheimer's disease. Alzheimer's disease is becoming tragically common. It is estimated that there are currently 18 million people worldwide with Alzheimer's disease. This figure is projected to nearly double by 2025 to 34 million people.

Considering the fact that there is at present no effective treatment for this fatal disease, it is an imperative to find new solutions to treat AD.

The sigma receptor has at least two subtypes, which may be discriminated by stereoselective isomers of these pharmaco-active drugs. SKF 10047 has nanomolar affinity for the sigma 1 (σ-1) site, and has micromolar affinity for the sigma (σ-2) site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.*, 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Sci.*, 1996, 93:8072-8077). The existence of sigma receptors in the CNS, immune and endocrine systems have suggested a likelihood that it may serve as link between the three systems.

Therefore, compounds binding to the sigma receptor and which are suitable for modulating these receptors are useful in the prevention and/or the treatment of diseases associated with the sigma receptor.

Recently it has been found that the sigma-1 receptor may be involved in the pathologenesis of Alzheimer's disease (Uchida at al., Am J Geriatr Psychiatry 2005; 13:1062-1066).

Thus, it was an objective of the present invention to provide new compounds for the use as active ingredients in medicaments. In particular, these active ingredients should be suitable to modulate the sigma receptor, more particularly the sigma-1 receptor.

Said objective was achieved by providing substituted bicyclic tetrahydropyrrolidine compounds of general formula (I) given below, their stereoisomers, corresponding salts and corresponding solvates thereof.

Thus, one of the aspect of the present invention relates to substituted bicyclic tetrahydropyrrolidine compounds of general formula (I)

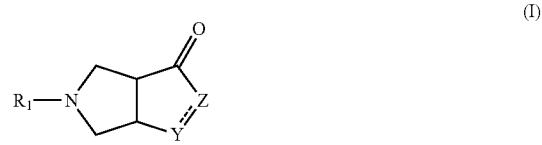

wherein
$R^1$ represents a hydrogen atom; an unbranched or branched, saturated or unsaturated, optionally at least mono-substituted aliphatic radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system; an optionally, at least mono-substituted benzhydryl group; a (C=O)—$R^2$ group; a (C=O)—$OR^3$ group; a ($SO_2$)—$R^4$ group; a (C=O)—$NR^5R^{5a}$ group;
wherein the bond between Y and Z may be unsaturated (Y=Z) or saturated (Y—Z);
in case of Y and Z being (Y=Z), Y represents CH and Z represents C—$R^6$; C—$CHR^7R^{7a}$; a C—(C=O)—$R^8$ group; a C—$CH_2(SO_2)$—$R^9$ group; a C—$CH_2(SO_2)$—$NR^{10}R^{10a}$ group; or a C—(C=O)—$NR^{10}R^{10a}$ group;
in case of Y and Z being (Y—Z), Y represents $CH_2$; C—$R^{11}R^{12}$; a CH—(C=O)—$R^{16}$ group; a CH—($SO_2$)—$R^{17}$ group; CH—($SO_2$)—$NR^{18}R^{18a}$ group; or a CH—(C=O)—$NR^{18}R^{18a}$ group and Z represents CH—$R^6$; CH—$CHR^7R^{7a}$; a CH—(C=O)—$R^8$ group; a CH—$CH_2(SO_2)$—$R^9$ group; a CH—$CH_2(SO_2)$—$NR^{10}R^{10a}$ group; or a CH—(C=O)—$NR^{10}R^{10a}$ group;
$R^2$, $R^3$, $R^4$, and $R^6$ represent a hydrogen atom; a linear or branched, saturated or unsaturated, optionally at least mono-substituted aliphatic group; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted;

a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^5$, $R^{5a}$, identical or different, represent a hydrogen atom; a linear or branched, saturated or unsaturated, optionally at least mono-substituted aliphatic group; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^7$, $R^{7a}$, identical or different, represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^8$, $R^9$, $R^{13}$, $R^{14}$, $R^{15}$, $R^{16}$ and $R^{17}$ represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^{10}$, $R^{10a}$, identical or different, represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^{11}$ and $R^{12}$, identical or different, represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system; a —(SO$_2$)—$R^{13}$-group; or a NR$^{14}$R$^{15}$-group;

$R^{18}$ and $R^{18a}$, identical or different, represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In this context it is preferred if one, more or all of the following provisos apply:

with the provisos that if Y and Z represent (CH=CH), $R^1$ may not represent a benzyl group;

if Y and Z represent

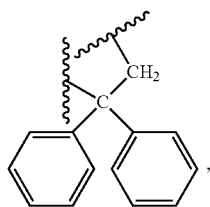 [SMILES: *CC(*)(c1ccccc1)c1ccccc1]

, $R^1$ may not be a —(C=O)—O-tert-butyl group, or a 1-(2-methoxyphenyl)ethan-2-one-2-yl group;

and/or if Y and Z represent ($CH_2$—$CH_2$), $R^1$ may not represent a hydrogen atom; a branched or unbranched, saturated or unsaturated aliphatic group; a cycloalkyl group; an unsubstituted benzyl group; an alkyl -cycloalkyl group; a substituted aryl group which is optionally condensed with a substituted unsaturated ring system; a —(C=O)—O-benzyl group;

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sultanate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or $^{15}N$-enriched nitrogen are within the scope of this invention.

The term "pharmacological tool" refers to the property of compounds of the invention through which they are particularly selective ligands for Sigma receptors which implies that compound of formula (I), described in this invention, can be used as a model for testing other compounds as sigma ligands, ex. a radioactive ligands being replaced, and can also be used for modeling physiological actions related to sigma receptors.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH4, but in particular (mono)- or (di)sodium, (mono)- or (di)potassium, magnesium or calcium salts.

These physiologically acceptable salts can also be formed with anions or acids and in the context of this invention is understood as meaning salts of at least one of the compounds used according to the invention—usually protonated, for example on the nitrogen—as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be in crystalline form or either as free compounds or as solvates and it is intended that those forms are within the scope of the present invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

The term "condensed" according to the present invention means that a ring or ring-system is attached to another ring or ring-system, whereby the terms "annulated" or "annelated" are also used by those skilled in the art to designate this kind of attachment.

The term "ring system" according to the present invention refers to ring system comprises saturated, unsaturated or aromatic carbocyclic ring system which contain optionally at least one heteroatom as ring member and which are optionally at least mono-substituted. Said ring systems may be condensed to other carbocyclic ring systems such as aryl groups, naphtyl groups, heteroaryl groups, cycloalkyl groups, etc.

"Optionally at least one heteroatom as ring member" is defined as having no heteroatom as ring member, one heteroatom as ring member or more than one heteroatom as ring member.

"Optionally at least mono-substituted" is defined as no hydrogen radical in the mentioned radical being substituted by another radical, e.g. Cl, F, etc., or one hydrogen radical in the mentioned radical being substituted by another radical, e.g. Cl, F, etc. or more than one hydrogen radical in the mentioned radical being substituted by another radical, e.g. Cl, F, etc. (polysubstituted).

"Optionally mono- or polysubstituted" is defined as no hydrogen radical in the mentioned radical being substituted by another radical, e.g. Cl, F, etc., or one hydrogen radical in the mentioned radical being substituted by another radical, e.g. Cl, F, etc. or more than one hydrogen radical in the mentioned radical being substituted by another radical, e.g. Cl, F, etc. (polysubstituted).

"Optionally substituted" is defined as no hydrogen radical in the mentioned radical being substituted by another radical, e.g. Cl, F, etc., or one hydrogen radical in the mentioned radical being substituted by another radical, e.g. Cl, F, etc. or more than one hydrogen radical in the mentioned radical being substituted by another radical, e.g. Cl, F, etc. (polysubstituted).

Cyclyl groups/radicals, as defined in the present invention, comprise any saturated, unsaturated or aromatic carbocyclic ring system which contain optionally at least one heteroatom as ring member and which are optionally at least monosubstituted. Cyclyl groups preferably comprise aryl, heteroaryl, cycloalkyl, heterocylcyl and/or spiro ring systems.

Heterocyclyl groups/radicals, as defined in the present invention, comprise any saturated, unsaturated or aromatic carbocyclic ring system which are optionally at least monosubstituted and which contain at least one heteroatom as ring member. Preferred heteroatoms for these heterocyclyl groups are N, S or O.

Aliphatic radicals/groups, as referred to in the present invention, are optionally mono- or polysubstituted and may be branched or unbranched, saturated or unsaturated. Unsaturated aliphatic groups, as defined in the present invention, include alkenyl and alkinyl radicals. Saturated aliphatic groups, as defined in the present invention, include alkyl radicals. Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl, n-heptyl, n-octyl, n-nonyl and n-decyl. Preferred substituents for aliphatic radicals, according to the present invention, are a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, oxo, (C=O)R', SR', SOR', $SO_2R'$, NHR', NR'R" whereby R' and optionally R" for each substituent independently represents a linear or branched $C_{1-6}$-alkyl group.

Alkyl radicals, as referred to in the present invention, are saturated aliphatic radicals. They may be linear or branched and are optionally substituted.

In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—; $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—; $(CH_2)_{4-5}$ is to be understood as meaning —$CH_2$—$CH_2$—$CH_2$—$CH_2$— and —$CH_2$—$CH_2$—$CH_2$—$CH_2$—$CH_2$—, etc.

Cycloalkyl radicals, as referred to in the present invention, are understood as meaning saturated and unsaturated (but not aromatic), cyclic hydrocarbons, which can optionally be unsubstituted, mono- or polysubstituted. In these radicals, for example $C_{3-4}$-cycloalkyl represents $C_3$- or $C_4$-cycloalkyl, $C_{3-5}$-cycloalkyl represents $C_3$-, $C_4$- or $C_5$-cycloalkyl, etc. With respect to cycloalkyl, the term also includes saturated cycloalkyls in which optionally at least one carbon atom may be replaced by a heteroatom, preferably S, N, P or O. However, mono- or polyunsaturated, preferably monounsaturated, cycloalkyls without a heteroatom in the ring also in particular fall under the term cycloalkyl as long as the cycloalkyl is not an aromatic system. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl.

Examples for cycloalkyl radicals preferably include but are not restricted to cyclopropyl, 2-methylcyclopropyl, cyclopropylmethyl, cyclobutyl, cyclopentyl, cyclopentylmethyl, cyclohexyl, cycloheptyl, cyclooctyl, acetyl, tert-butyl, adamantyl, pyrroline, pyrrolidine, pyrrolidineone, pyrazoline, pyrazolinone, oxopyrazolinone, aziridine, acetidine, tetrahydropyrrole, oxirane, oxetane, dioxetane, tetrahydrofurane, dioxane, dioxolane, oxathiolane, oxazolidine, thiirane, thietane, thiolane, thiane, thiazolidine, piperidine, piperazine or morpholine.

Cycloalkyl radicals, as defined in the present invention, are optionally mono- or polysubstituted by substitutents independently selected from a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, oxo, (C=O)R', SR', SOR', $SO_2R'$, NHR', NR'R" whereby R' and optionally R" for each substituent independently represents a linear or branched $C_{1-6}$-alkyl group.

An aryl radical, as referred to in the present invention, is understood as meaning ring systems with at least one aromatic ring but without heteroatoms even in only one of the rings. These aryl radicals may optionally be mono- or polysubstituted by substitutents independently selected from a $C_{1-4}$ alkyl group, a linear or branched $C_{1-6}$ alkoxy group, an optionally at least mono-substituted phenyl group, F, Cl, I, Br, $CF_3$, $CH_2F$, $CHF_2$, CN, OH, SH, $NH_2$, oxo, (C=O)R', SR', SOR', $SO_2R'$, N(C=O)—OR', NHR', NR'R" whereby R' and optionally R" for each substituent independently represents a linear or branched $C_{1-6}$-alkyl group. Preferred examples of aryl radicals include but are not restricted to phenyl, naphthyl, fluoranthenyl, fluorenyl, tetralinyl or indanyl or anthracenyl radicals, which may optionally be mono- or polysubstituted, if not defined otherwise.

An alkyl-aryl radical, as defined in the present invention, comprises a linear or branched, optionally at least monosubstituted alkyl chain which is bonded to an aryl group, as defined above. A preferred alkyl-aryl radical is a benzyl group, wherein the alkyl chain is optionally branched or substituted. Preferred substituents for alky-aryl radicals, according to the present invention, are F, Cl, Br, I, $NH_2$, SH, OH, $SO_2$, $CF_3$, carboxy, amido, cyano, carbamyl, nitro, phenyl, benzyl, —$SO_2NH_2$, $C_{1-6}$ alkyl and/or $C_{1-6}$-alkoxy.

A heteroaryl radical is understood as meaning heterocyclic ring systems which have at least one aromatic ring and may optionally contain one or more heteroatoms from the group consisting of nitrogen, oxygen and/or sulfur and may optionally be mono- or polysubstituted by substitutents independently selected from a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, oxo, (C=O)R', SR', SOR', $SO_2R'$, NHR', NR'R" whereby R' and optionally R" for each substitutent independently represents a linear or branched $C_{1-6}$-alkyl group. Preferred examples of heteroaryls include but are not restricted to furan, benzofuran, thiophene, benzothiophene, pyrrole, pyridine, pyrimidine, pyridazine, pyrazine, quinoline, isoquinoline, phthalazine, benzo-1,2,5-thiadiazole, benzothiazole, indole, benzotriazole, benzodioxolane, benzodioxane, benzimidazole, carbazole and quinazoline.

An alkyl-heteroaryl (or alkyl-heterocyclyl) radical, as defined in the present invention, comprises a linear or branched, optionally at least mono-substituted alkyl chain which is bonded to an heteroaryl (heterocyclyl) group, as defined above.

With respect to compounds of general formula (I) of the present invention, Y and Z may form an unsaturated (Y=Z) or a saturated (Y—Z) bond which is illustrated below.

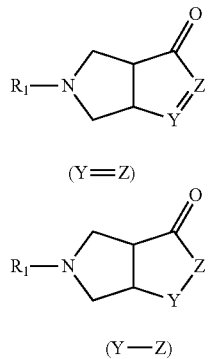

(Y=Z)

(Y—Z)

A preferred embodiment of the present invention are compounds of general formula (I) as defined above,
wherein
$R^1$ represents a hydrogen atom; an unbranched or branched, saturated or unsaturated, optionally at least mono-substituted aliphatic radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system; an optionally, at least mono-substituted benzhydryl group; a (C=O)—$R^2$ group; a (C=O)—$OR^3$ group; a ($SO_2$)—$R^4$ group; a (C=O)—$NR^5R^{5a}$ group;
wherein the bond between Y and Z is unsaturated (Y=Z), with Y representing CH and Z representing C—$R^6$; C—$CHR^7R^{7a}$; a C—(C=O)—$R^8$ group; a C—$CH_2$($SO_2$)—$R^9$ group; a C—$CH_2$($SO_2$)—$NR^{10}R^{10a}$ group; or a C—(C=O)—$NR^{10}R^{10a}$ group;
$R^2$, $R^3$, $R^4$, $R^5$, $R^{5a}$, $R^6$, $R^7$, $R^{7a}$, $R^8$, $R^9$, $R^{10}$ and $R^{10a}$, have the meaning as defined above.
In this context it is preferred if the following proviso applies:
with the proviso that if Z represents a CH group,
$R^1$ may not represent a benzyl group.

Another preferred embodiment of the present invention are compounds of general formula (I) as defined above,
wherein
$R^1$ represents a hydrogen atom; an unbranched or branched, saturated or unsaturated, optionally at least mono-substituted aliphatic radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system; an optionally, at least mono-substituted benzhydryl group; a (C=O)—$R^2$ group; a (C=O)—$OR^3$ group; a ($SO_2$)—$R^4$ group; a (C=O)—$NR^5R^{5a}$ group;
wherein the bond between Y and Z is saturated (Y—Z), with Y representing $CH_2$; C—$R^{11}R^{12}$; a CH—(C=O)—$R^{16}$ group; a CH—($SO_2$)—$R^{17}$ group; CH—($SO_2$)—$NR^{18}R^{18a}$ group; or a CH—(C=O)—$NR^{18}R^{18a}$ group and Z representing CH—$R^6$; CH—$CHR^7R^{7a}$; a CH—(C=O)—$R^8$ group; a CH—$CH_2$($SO_2$)—$R^9$ group; a CH—$CH_2$($SO_2$)—$NR^{10}R^{10a}$ group; or a CH—(C=O)—$NR^{10}R^{10a}$ group;
$R^2$, $R^3$, $R^4$, $R^5$, $R^{5a}$, $R^6$, $R^7$, $R^{7a}$, $R^8$, $R^9$, $R^{10}$, $R^{10a}$, $R^{11}$, $R^{12}$, $R^{13}$, $R^{14}$, $R^{15}$, $R^{16}$, $R^{17}$, $R^{18}$ and $R^{18a}$ have the meaning as defined above;
In this context it is preferred if one, more or all of the following provisos apply:
with the provisos that
if Y and Z represent

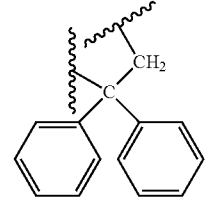 [SMILES: *CC(*)(c1ccccc1)c1ccccc1]

$R^1$ may not be a —(C=O)—O-tert-butyl group, or a 1-(2-methoxyphenyl)ethan-2-one-2-yl group;
and/or
if Y and Z represent ($CH_2$—$CH_2$), $R^1$ may not represent a hydrogen atom; a branched or unbranched, saturated or unsaturated aliphatic group; a cycloalkyl group; an unsubstituted benzyl group; an alkyl-cycloalkyl group; a substituted aryl group which may be condensed with a substituted unsaturated ring system; or a —(C═O)—O-benzyl group.

Another preferred embodiment of the present invention are compounds of general formula (I) as defined above, wherein $R^1$ represents a hydrogen atom; an unbranched or branched, saturated or unsaturated, optionally at least mono-substituted aliphatic radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; an optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system; an optionally, at least mono-substituted benzhydryl group; a (C═O)—$R^2$ group; a (C═O)—$OR^3$ group; a ($SO_2$)—$R^4$ group; a (C═O)—$NR^5R^{5a}$ group;

wherein the bond between Y and Z is unsaturated (Y═Z), with Y representing CH and Z representing C—$R^6$; C—$CHR^7R^{7a}$; a C—(C═O)—$R^8$ group; a C—$CH_2$($SO_2$)—$R^9$ group; a C—$CH_2$($SO_2$)—$NR^{10}R^{10a}$ group; or a C—(C═O)—$NR^{10}R^{10a}$ group;

$R^2$, $R^3$, $R^4$, $R^5$, $R^{5a}$, $R^7$, $R^{7a}$, $R^8$, $R^9$, $R^{10}$ and $R^{10a}$, have the meaning as defined above;

$R^6$ represents a linear or branched, saturated or unsaturated, optionally at least mono-substituted aliphatic group; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system.

Another preferred embodiment of the present invention are compounds of general formula (I) as defined above, wherein $R^1$ represents a hydrogen atom; an unbranched or branched, saturated or unsaturated, optionally at least mono-substituted aliphatic radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system; an optionally, at least mono-substituted benzhydryl group; a (C═O)—$R^2$ group; a (C═O)—$OR^3$ group; a ($SO_2$)—$R^4$ group; a (C═O)—$NR^5R^{5a}$ group;

wherein the bond between Y and Z is saturated (Y—Z), with Y representing $CH_2$; C—$R^{11}R^{12}$; a CH—(C═O)—$R^{16}$ group; a CH—($SO_2$)—$R^{17}$ group; CH—($SO_2$)—$NR^{18}R^{18a}$ group; or a CH—(C═O)—$NR^{18}R^{18a}$ group and Z representing CH—$R^6$; CH—$CHR^7R^{7a}$; a CH—(C═O)—$R^8$ group; a CH—$CH_2$($SO_2$)—$R^9$ group; a CH—$CH_2$($SO_2$)—$NR^{10}R^{10a}$ group; or a CH—(C═O)—$NR^{10}R^{10a}$ group;

$R^2$, $R^3$, $R^4$, $R^5$, $R^{5a}$, $R^7$, $R^{7a}$, $R^8$, $R^9$, $R^{10}$, $R^{10a}$, $R^{11}$, $R^{12}$, $R^{13}$, $R^{14}$, $R^{15}$ $R^{16}$, $R^{17}$, $R^{18}$ and $R^{18a}$ have the meaning as defined above;

$R^6$ represents a linear or branched, saturated or unsaturated, optionally at least mono-substituted aliphatic group; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^{11}$ and $R^{12}$, identical or different, represents a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cycloalkyl group, which may be condensed with an optionally at least mono-substituted mono- or polycyclic ring system; an optionally at least mono-substituted aryl group, which may be condensed with an optionally at least mono-substituted mono- or polycyclic ring system; an optionally at least mono-substituted heteroaryl group, which may be condensed with an optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system; a —($SO_2$)—$R^{13}$-group; or a —$NR^{14}R^{15}$-group; with the condition that $R^{11}$ and $R^{12}$ may not at the same time represent a phenyl group or may not at the same time represent a hydrogen atom.

Another preferred embodiment of the present invention are compounds of general formula (I) as defined above, wherein $R^1$ represents a hydrogen atom; an unbranched or branched $C_{1-6}$ alkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2$R', NHR', NR'R" whereby R' and optionally R" for each substituent independently represents linear or branched $C_{1-6}$-alkyl group; a saturated or unsaturated cycloalkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2$R', NHR', NR'R" whereby R' and optionally R" for each substituent independently represents linear or branched $C_{1-6}$-alkyl group, and which may be condensed with an optionally at least mono-substituted mono- or polycyclic ring system with substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2$R', NHR', NR'R" whereby R' and optionally R" for each substituent independently represents linear or branched $C_{1-6}$-alkyl group; an aryl group, which is optionally substituted by one or more substituents independently selected from the group consisting of a $C_{1-4}$ alkyl group, a linear or branched $C_{1-6}$ alkoxy group, a N—(C=O)O-tert-butyl group, an optionally F, Cl, I, Br or $CF_3$-substituted phenyl group, F, Cl, I, Br, $CF_3$, $CH_2F$, $CHF_2$, CN, OH, SH, $NH_2$, (C=O)R', SR', SOR', $SO_2$R', NHR', NR'R" whereby R' and optionally R" for each substituent independently represents linear or branched $C_{1-6}$-alkyl group, and which may be condensed with an optionally at least mono-substituted mono- or polycyclic ring system with substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2$R', NHR', NR'R" whereby R' and optionally R" for each substituent independently represents linear or branched $C_{1-6}$-alkyl group; a heteroaryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2$R', NHR', NR'R" whereby R' and optionally R" for each substituent independently represents linear or branched $C_{1-6}$-alkyl group, and which may be condensed with an optionally at least mono-substituted mono- or polycyclic ring system with substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, (C=O)R', SR', SOR', $SO_2$R', NHR', NR'R" whereby R' and optionally R" for each substituent independently represents linear or branched $C_{1-6}$-alkyl group; a branched or unbranched alkyl-cycloalkyl group in which either the alkyl group and/or the cycloalkyl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2$R', NHR', NR'R" whereby R' and optionally R" for each substituent independently represents linear or branched $C_{1-6}$-alkyl group; an alkyl-aryl group in which either the alkyl group and/or the aryl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2$R', NHR', NR'R" whereby R' and optionally R" for each substituent independently represents linear or branched $C_{1-6}$-alkyl group and in which the aryl group may be condensed with another, optionally at least mono-substituted mono- or polycyclic ring system; a branched or unbranched, saturated or unsaturated alkyl-heterocyclyl group in which either the alkyl group and/or the heterocyclyl group is substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2$R', NHR', NR'R" whereby R' and optionally R" for each substituent independently represents linear or branched $C_{1-6}$-alkyl group and in which the heterocyclyl group is optionally condensed with another, at least mono-substituted mono- or polycyclic ring system; an optionally, at least mono-substituted benzhydryl group; a (C=O)—$R^2$ group; a (C=O)—$OR^3$ group; a $(SO_2)$—$R^4$ group; a (C=O)—$NR^5R^{5a}$ group;

wherein the bond between Y and Z is unsaturated (Y=Z), with Y representing CH and Z representing C—$R^6$; C—$CHR^7R^{7a}$, a C—(C=O)—$R^8$ group; a C—$CH_2$$(SO_2)$—$R^9$ group; a C—$CH_2(SO_2)$—$NR^{10}R^{10a}$ group; or a C—(C=O)—$NR^{10}R^{10a}$ group;

$R^2$, $R^3$, $R^4$, $R^5$, $R^{5a}$, $R^7$, $R^{7a}$, $R^8$, $R^9$, $R^{10}$ and $R^{10a}$ have the meaning as defined above;

$R^6$ has the meaning as defined above.

Another preferred embodiment of the present invention are compounds of general formula (I) as defined above, wherein $R^1$ represents an unbranched or branched $C_{1-6}$ alkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2$R', NHR', NR'R" whereby R' and optionally R" for each substituent independently represents linear or branched $C_{1-6}$-alkyl group; a saturated or unsaturated cycloalkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2$R', NHR', NR'R" whereby R' and optionally R" for each substituent independently represents linear or branched $C_{1-6}$-alkyl group, and which may be condensed with an optionally at least mono-substituted mono- or polycyclic ring system with substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2$R', NHR', NR'R" whereby R' and optionally R" for each substituent independently represents linear or branched $C_{1-6}$-alkyl group; an aryl group, which is optionally substituted by one or more substituents independently selected from the group consisting of a $C_{1-4}$ alkyl group, a linear or branched $C_{1-6}$ alkoxy group, a N—(C=O)O-tert-butyl group, an optionally F, Cl, I, Br or $CF_3$-substituted phenyl group, F, Cl, I, Br, $CF_3$, $CH_2F$, $CHF_2$, CN, OH, SH, $NH_2$, (C=O)R', SR', SOR', $SO_2R'$, NHR', NR'R" whereby R' and optionally R" for each substitutent independently represents linear or branched $C_{1-6}$-alkyl group, and which may be condensed with an optionally at least mono-substituted mono- or polycyclic ring system with substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, NHR', NR'R" whereby R' and optionally R" for each substitutent independently represents linear or branched $C_{1-6}$-alkyl group; a heteroaryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, NHR', NR'R" whereby R' and optionally R" for each substitutent independently represents linear or branched $C_{1-6}$-alkyl group, and which may be condensed with an optionally at least mono-substituted mono- or polycyclic ring system with substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, NHR', NR'R" whereby R'and optionally R" for each substitutent independently represents linear or branched $C_{1-6}$-alkyl group; a branched or unbranched alkyl-cycloalkyl group in which either the alkyl group and/or the cycloalkyl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (CO)R', SR', SOR', $SO_2R'$, NHR', NR'R"whereby R' and optionally R" for each substitutent independently represents linear or branched $C_{1-6}$-alkyl group; an alkyl-aryl group in which either the alkyl group and/or the aryl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (CO)R', SR', SOR', $SO_2R'$, NHR', NR'R" whereby R' and optionally R" for each substitutent independently represents linear or branched $C_{1-6}$-alkyl group and in which the aryl group may be condensed with another, optionally at least mono-substituted mono- or polycyclic ring system; a branched or unbranched, saturated or unsaturated alkyl-heterocyclyl group in which either the alkyl group and/or the heterocyclyl group is substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, NHR', NR'R" whereby R' and optionally R" for each substitutent independently represents linear or branched $C_{1-6}$-alkyl group and in which the heterocyclyl group is optionally condensed with another, at least mono-substituted mono- or polycyclic ring system; an optionally, at least mono-substituted benzhydryl group; a (C=O)—$R^2$ group; a (C=O)—$OR^3$ group; a $(SO_2)$—$R^4$ group; a (C=O)—$NR^5R^{5a}$ group;

wherein the bond between Y and Z is saturated (Y=Z), with Y representing a C—$R^{11}R^{12}$; a CH—(C=O)—$R^{16}$ group; a CH—$(SO_2)$—$R^{17}$ group; CH—$(SO_2)$—$NR^{18}R^{18a}$ group; or a CH—(C=O)—$NR^{18}R^{18a}$ group and Z representing CH—$R^6$; CH—$CHR^7R^{7a}$; a CH—(C=O)—$R^8$ group; a CH—$CH_2(SO_2)$—$R^9$ group; a CH—$CH_2(SO_2)$—$NR^{10}R^{10a}$ group; or a CH—(C=O)—$NR^{10}R^{10a}$ group;

$R^8$, $R^{11}$ and $R^{12}$ have the meaning as defined above;
$R^2$, $R^3$, $R^4$, $R^5$, $R^{5a}$, $R^7$, $R^{7a}$, $R^8$, $R^9$, $R^{10}$, $R^{10a}$, $R^{13}$, $R^{14}$, $R^{15}$ $R^{16}$, $R^{17}$, $R^{18}$ and $R^{18a}$ have the meaning as defined above.

Another preferred embodiment of the present invention are compounds of general formula (I) as defined above, wherein $R^2$, $R^3$, and $R^4$ represent a hydrogen atom; an unbranched or branched $C_{1-6}$ alkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a saturated or unsaturated cycloalkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an aryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a heteroaryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched alkyl-cycloalkyl group in which either the alkyl group and/or the cycloalkyl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an alkyl-aryl group in which either the alkyl group and/or the aryl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched, saturated or unsaturated alkyl-heterocyclyl group in which either the alkyl group and/or the heterocyclyl group is substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$.

Another preferred embodiment of the present invention are compounds of general formula (I) as defined above, wherein $R^5$ and $R^{5a}$, identical or different, represent a hydrogen atom; an unbranched or branched $C_{1-6}$ alkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a saturated or unsaturated cycloalkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an aryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a heteroaryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched alkyl-cycloalkyl group in which either the alkyl group and/or the cycloalkyl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an alkyl-aryl group in which either the alkyl group and/or the aryl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched, saturated or unsaturated alkyl-heterocyclyl group in which either the alkyl group and/or the heterocyclyl group is substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$.

Another preferred embodiment of the present invention are compounds of general formula (I) as defined above,
wherein
$R^7$ and $R^{7a}$, identical or different, represent a hydrogen atom; an unbranched or branched $C_{1-6}$ alkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an unbranched or branched $C_{1-6}$ alkoxy group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a saturated or unsaturated cycloalkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an aryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a heteroaryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched alkyl-cycloalkyl group in which either the alkyl group and/or the cycloalkyl group is optionally substituted by one or more substituents independently selected from the group consisting of a $C_{1-6}$ alkyl group, a linear or branched $C_{1-4}$ alkoxy group, F, Cl, I, Br, $CF_3$, $CH_2F$, $CHF_2$, CN, OH, SH, $NH_2$; an alkyl-aryl group in which either the alkyl group and/or the aryl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched, saturated or unsaturated alkyl-heterocyclyl group in which either the alkyl group and/or the heterocyclyl group is substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$.

Another preferred embodiment of the present invention are compounds of general formula (I) as defined above,
wherein
$R^8, R^9, R^{13}, R^{14}, R^{15}, R^{16}$ and $R^{17}$ represent a hydrogen atom; an unbranched or branched $C_{1-6}$ alkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an unbranched or branched $C_{1-6}$ alkoxy group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a saturated or unsaturated cycloalkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an aryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a heteroaryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched alkyl-cycloalkyl group in which either the alkyl group and/or the cycloalkyl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an alkyl-aryl group in which either the alkyl group and/or the aryl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched, saturated or unsaturated alkyl-heterocyclyl group in which either the alkyl group and/or the heterocyclyl group is substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$.

Another preferred embodiment of the present invention are compounds of general formula (I) as defined above,
wherein
$R^{10}$ and $R^{10a}$, identical or different, represent a hydrogen atom; an unbranched or branched $C_{1-6}$ alkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an unbranched or branched $C_{1-6}$ alkoxy group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a saturated or unsaturated cycloalkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an aryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a heteroaryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched alkyl-cycloalkyl group in which either the alkyl group and/or the cycloalkyl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an alkyl-aryl group in which either the alkyl group and/or the aryl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched, saturated or unsaturated alkyl-heterocyclyl group in which either the alkyl group and/or the heterocyclyl group is substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$.

Yet, another preferred embodiment of the present invention are compounds of general formula (I) as defined above, wherein $R^{11}$ and $R^{12}$, identical or different, represent a hydrogen atom; an unbranched or branched $C_{1-6}$ alkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an unbranched or branched $C_{1-6}$ alkoxy group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a saturated or unsaturated cycloalkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an aryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a heteroaryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched alkyl-cycloalkyl group in which either the alkyl group and/or the cycloalkyl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an alkyl-aryl group in which either the alkyl group and/or the aryl group is optionally substituted by one or more substituents independently selected from the group consisting of a $C_{1-4}$ alkyl group, a linear or branched $C_{1-4}$ alkoxy group, F, Cl, I, Br, $CF_3$, $CH_2F$, $CHF_2$, CN, OH, SH, $NH_2$; a branched or unbranched, saturated or unsaturated alkyl-heterocyclyl group in which either the alkyl group and/or the heterocyclyl group is substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a $(SO_2)$—$R^{13}$-group; or a $NR^{14}R^{15}$-group; with the condition that $R^{11}$ and $R^{12}$ may not at the same time represent a phenyl group or may not at the same time represent a hydrogen atom.

Yet, another preferred embodiment of the present invention are compounds of general formula (I) as defined above, wherein $R^{18}$ and $R^{18a}$, identical or different, represent a hydrogen atom; an unbranched or branched $C_{1-6}$ alkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an unbranched or branched $C_{1-6}$ alkoxy group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a saturated or unsaturated cycloalkyl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an aryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a heteroaryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched alkyl-cycloalkyl group in which either the alkyl group and/or the cycloalkyl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; an alkyl-aryl group in which either the alkyl group and/or the aryl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$; a branched or unbranched, saturated or unsaturated alkyl-heterocyclyl group in which either the alkyl group and/or the heterocyclyl group is substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$.

A highly preferred embodiment of the present invention are compounds of general formula (I) as defined above, wherein $R^1$ represents an alkyl-aryl group in which either the alkyl group and/or the aryl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, NHR', NR'R" whereby R' and optionally R" for each substitutent independently represents linear or branched $C_{1-6}$-alkyl group and in which the aryl group may be condensed with another, optionally at least mono-substituted mono- or polycyclic ring system; a benzhydryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH or SH;

wherein the bond between Y and Z is unsaturated (Y=Z), with Y representing CH and Z representing a C—$R^6$ group;

$R^6$ represents an unbranched or branched $C_{1-6}$ alkyl group, which is optionally substituted by one or more substituents independently selected from the group consisting of a F, Cl, I, Br, $CF_3$, $CH_2F$, $CHF_2$, CN, OH, SH, $NH_2$; an aryl group, which is optionally substituted by one or more substituents independently selected from the group consisting of a $C_{1-4}$ alkyl group; an optionally at least mono-substituted phenyl group; a linear or branched $C_{1-6}$ alkoxy group; F, Cl, I, Br, $CF_3$, $CH_2F$, $CHF_2$, CN, OH, SH, $NH_2$, (C=O)R', SOR', $SO_2R'$, N(C=O)—OR', NHR', NR'R" whereby R' and optionally R" for each substitutent independently represents linear or branched $C_{1-6}$-alkyl group; an alky-aryl group, in which either the alkyl group and/or the aryl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)

R', SR', SOR', SO$_2$R', NHR', NR'R" whereby R' and optionally R" for each substituent independently represents linear or branched C$_{1-6}$-alkyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

A highly preferred embodiment of the present invention are compounds of general formula (I) as defined above, wherein R$^1$ represents an alkyl-aryl group in which either the alkyl group and/or the aryl group is optionally substituted by one or more substituents independently selected from the group consisting of a C$_{1-4}$ alkyl group, a linear or branched C$_{1-6}$ alkoxy group, F, Cl, I, Br, CF$_3$, CH$_2$F, CHF$_2$, CN, OH, SH, NH$_2$, (C═O)R', SR', SOR', SO$_2$R', NHR', NR'R" whereby R' and optionally R" for each substituent independently represents linear or branched C$_{1-6}$-alkyl group and in which the aryl group may be condensed with another, optionally at least mono-substituted mono- or polycyclic ring system; a benzhydryl group, which is optionally substituted by one or more substituents independently selected from the group consisting of a C$_{1-4}$ alkyl group, a linear or branched C$_{1-4}$ alkoxy group, F, Cl, I, Br, CF$_3$, CH$_2$F, CHF$_2$, CN, OH or SH;

wherein the bond between Y and Z is saturated (Y—Z), with Y representing CH$_2$; C—R$^{11}$R$^{12}$; and Z representing CH—R$^6$;

R$^6$ represents an unbranched or branched C$_{1-6}$ alkyl group, which is optionally substituted by one or more substituents independently selected from the group consisting of a F, Cl, I, Br, CF$_3$, CH$_2$F, CHF$_2$, CN, OH, SH, NH$_2$; an aryl group, which is optionally substituted by one or more substituents independently selected from the group consisting of a C$_{1-4}$ alkyl group; an optionally at least mono-substituted phenyl group; a linear or branched C$_{1-6}$ alkoxy group; F, Cl, I, Br, CF$_3$, CH$_2$F, CHF$_2$, CN, OH, SH, NH$_2$, (C═O)R', SR', SOR', SO$_2$R', N(C═O)—OR', NHR', NR'R" whereby R' and optionally R" for each substituent independently represents linear or branched C$_{1-6}$-alkyl group; an alky-aryl group in which either the alkyl group and/or the aryl group is optionally substituted by one or more substituents independently selected from the group consisting of a C$_{1-4}$ alkyl group, a linear or branched C$_{1-6}$ alkoxy group, F, Cl, I, Br, CF$_3$, CH$_2$F, CHF$_2$, CN, OH, SH, NH$_2$, (C═O)R', SR', SOR', SO$_2$R', NHR', NR'R" whereby R' and optionally R" for each substituent independently represents linear or branched C$_{1-6}$-alkyl group;

R$^{11}$ and R$^{12}$, identical or different, represent a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cycloalkyl group, which may be condensed with an optionally at least mono-substituted mono- or polycyclic ring system; an optionally at least mono-substituted aryl group, which may be condensed with an optionally at least mono-substituted mono- or polycyclic ring system; an optionally at least mono-substituted heteroaryl group, which may be condensed with an optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system; with the condition that R$^{11}$ and R$^{12}$ may not at the same time represent a phenyl group or may not at the same time represent a hydrogen atom;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Also very preferred are compounds of general formula (I), wherein

R$^1$ represents
an alkyl-aryl group in which either the alkyl group and/or the aryl group is optionally substituted by one or more substituents independently selected from the group consisting of a C$_{1-4}$ alkyl group, a linear or branched C$_{1-6}$ alkoxy group, F, Cl, I, Br, CF$_3$, CH$_2$F, CHF$_2$, CN, OH, SH, NH$_2$, (C═O)R', SOR', SO$_2$R', NHR', NR'R" whereby R' and optionally R" for each substituent independently represents linear or branched C$_{1-6}$-alkyl group and in which the aryl group may be condensed with another, optionally at least mono-substituted mono- or polycyclic ring system;
a benzhydryl group, which is optionally substituted by one or more substituents independently selected from the group consisting of a C$_{1-4}$ alkyl group, a linear or branched C$_{1-6}$ alkoxy group, F, Cl, I, Br, CF$_3$, CH$_2$F, CHF$_2$, CN, OH or SH;

wherein the bond between Y and Z is saturated (Y—Z), with Y representing CH$_2$; C—R$^{11}$R$^{12}$; and Z representing CH—R$^6$;
or
wherein the bond between Y and Z is unsaturated (Y═Z), with Y representing CH and Z representing a C—R$^6$ group;

R$^6$ represents
an unbranched or branched C$_{1-6}$ alkyl group, which is optionally substituted by one or more substituents independently selected from the group consisting of a F, Cl, I, Br, CF$_3$, CH$_2$F, CHF$_2$, CN, OH, SH, NH$_2$;
an aryl group, which is optionally substituted by one or more substituents independently selected from the group consisting of a C$_{1-4}$ alkyl group; an optionally at least mono-substituted phenyl group; a linear or branched C$_{1-6}$ alkoxy group; F, Cl, I, Br, CF$_3$, CH$_2$F, CHF$_2$, CN, OH, SH, NH$_2$, (C═O)R', SR', SOR', SO$_2$R', N(C═O)—OR', NHR', NR'R" whereby R' and optionally R"for each substituent independently represents linear or branched C$_{1-6}$-alkyl group;
an alky-aryl group in which either the alkyl group and/or the aryl group is optionally substituted by one or more substituents independently selected from the group consisting of a C$_{1-4}$ alkyl group, a linear or branched C$_{1-6}$ alkoxy group, F, Cl, I, Br, CF$_3$, CH$_2$F, CHF$_2$, CN, OH, SH, NH$_2$, (C═O)R', SR', SOR', SO$_2$R', NHR', NR'R" whereby R' and optionally R" for each substituent independently represents linear or branched C$_{1-6}$-alkyl group; or
trimethylsilyl;

R$^{11}$ and R$^{12}$ independently from another represent hydrogen a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cycloalkyl group, which may be condensed with an optionally at least mono-substituted mono- or polycyclic ring system; an optionally at least mono-substituted aryl group, which may be condensed with an optionally at least mono-substituted mono- or polycyclic ring system; an optionally at least mono-substituted alkyl-aryl group, which may be condensed with an optionally at least mono-substituted mono- or polycyclic ring system; an optionally at least mono-substituted heteroaryl group, which may be condensed with an optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system; with the condition that $R^{11}$ and $R^{12}$ may not at the same time represent a phenyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Also very preferred are compounds of general formula (I), wherein $R^1$ represents an alkyl-aryl group in which either the alkyl group and/or the aryl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, NHR', NR'R" whereby R' and optionally R" for each substitutent independently represents linear or branched $C_{1-6}$-alkyl group and in which the aryl group may be condensed with another, optionally at least mono-substituted mono- or polycyclic ring system;

a benzhydryl group, which is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH or SH;

wherein the bond between Y and Z is saturated (Y—Z), with Y representing $CH_2$; C—$R^{11}R^{12}$; and Z representing CH—$R^6$;

or wherein the bond between Y and Z is unsaturated (Y=Z), with Y representing CH and Z representing a C—$R^6$ group;

$R^6$ represents an unbranched or branched $C_{1-6}$ alkyl group, which is optionally substituted by one or more substituents independently selected from the group consisting of a F, Cl, I, Br, $CF_3$, $CH_2F$, $CHF_2$, CN, OH, SH, $NH_2$;

an aryl group, which is optionally substituted by one or more substituents independently selected from the group consisting of a $C_{1-4}$ alkyl group; an optionally at least mono-substituted phenyl group; a linear or branched $C_{1-6}$ alkoxy group; F, Cl, I, Br, $CF_3$, $CH_2F$, $CHF_2$, CN, OH, SH, $NH_2$, (C=O)R', SR', SOR', $SO_2R'$, N(C=O)—OR', NHR', NR'R" whereby R' and optionally R"for each substitutent independently represents linear or branched $C_{1-6}$-alkyl group;

an alky-aryl group in which either the alkyl group and/or the aryl group is optionally substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, NHR', NR'R" whereby R' and optionally R" for each substitutent independently represents linear or branched $C_{1-6}$-alkyl group; or trimethylsilyl;

$R^{11}$ represents hydrogen;

$R^{12}$ represents hydrogen; a linear or branched, saturated or unsaturated, optionally at least mono-substituted $C_{1-6}$-aliphatic group; an unbranched or branched, saturated or unsaturated, optionally at least mono-substituted $C_{1-6}$-alkoxy radical; a saturated or mono-unsaturated, optionally at least mono-substituted $C_{4-8}$-cycloalkyl group; a saturated or mono-unsaturated, optionally at least mono-substituted alkyl-$C_{4-8}$-cycloalkyl group; an optionally at least mono-substituted aryl group; an optionally at least mono-substituted alkyl-aryl group; an optionally at least mono-substituted heteroarlyl group; an optionally at least mono-substituted alkyl-heterocyclyl group;

preferably represents a linear or branched, saturated or unsaturated, optionally at least mono-substituted $C_{1-6}$-aliphatic group; an optionally at least mono-substituted aryl group; or an optionally at least mono-substituted heteroaryl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Most highly preferred are compounds of general formula (I) as described above, selected from the group consisting of:

[1] 2-benzyl-5-phenyl-(3a,6a-cis)-1,2,3,3a-tetrahydrocyclopenta[c]pyrrol-4(6aH)-one,

[2] 5-phenyl-2-((S)-1-phenylethyl)-(3a,6a-cis)-1,2,3,3a-tetrahydrocyclopenta[c]pyrrol-4(6aH)-one,

[3] 2-(4-methoxybenzyl)-5-phenyl-(3a,6a-cis)-1,2,3,3a-tetrahydrocyclopenta[c]pyrrol-4(6aH)-one,

[4] 2-benzyl-5-(4-fluorophenyl)-(3a,6a-cis)-1,2,3,3a-tetrahydrocyclopenta[c]pyrrol-4(6aH)-one,

[5] 2-benzyl-5-(4-ethylphenyl)-(3a,6a-cis)-1,2,3,3a-tetrahydrocyclopenta[c]pyrrol-4(6aH)-one,

[6] 2-benzyl-5-(2-chlorophenyl)-(3a,6a-cis)-1,2,3,3a-tetrahydrocyclopenta[c]pyrrol-4(6aH)-one,

[7] 2-benzyl-5-(4-chlorophenyl)-(3a,6a-cis)-1,2,3,3a-tetrahydrocyclopenta[c]pyrrol-4(6aH)-one,

[8] 2-benzyl-5-(3-chlorophenyl)-(3a,6a-cis)-1,2,3,3a-tetrahydrocyclopenta[c]pyrrol-4(6aH)-one,

[9] 2-benzyl-5-(4-methoxyphenyl)-(3a,6a-cis)-1,2,3,3a-tetrahydrocyclopenta[c]pyrrol-4(6aH)-one,

[10] 2-benzyl-5-(biphenyl-4-yl)-(3a,6a-cis)-1,2,3,3a-tetrahydrocyclopenta[c]pyrrol-4(6aH)-one,

[11] 2-benzyl-5-(4-tert-butylcarbamatephenyl)-(3a,6a-cis)-1,2,3,3a-tetrahydrocyclopenta[c]pyrrol-4(6aH)-one,

[12] 2-benzyl-5-butyl-(3a,6a-cis)-1,2,3,3a-tetrahydrocyclopenta[c]pyrrol-4(6aH]-one,

[13] 2-benzhydryl-5-phenyl-(3a,6a-cis)-1,2,3,3a-tetrahydrocyclopenta[c]pyrrol-4(6aH)-one,

[14] 2,5-dibenzyl-(3a,6a-cis)-1,2,3,3a-tetrahydrocyclopenta[c]pyrrol-4(6aH)-one,

[15] 2-(4-fluorobenzyl)-5-phenyl-(3a,6a-cis)-1,2,3,3a-tetrahydrocyclopenta[c]pyrrol-4(6aH)-one,

[18] 2-benzyl-5-(trimethylsilyl)-(3a,6a-cis)-1,2,3,3a-tetrahydrocyclopenta[c]pyrrol-4(6aH)-one;
[17] 2-benzyl-(3a,6a-cis)-1,2,3,3a-tetrahydrocyclopenta[c]pyrrol-4(6aH)-one;
[18] 2-benzyl-5-tert-butyl-(3a,6a-cis)-1,2,3,3a-tetrahydrocyclopenta[c]pyrrol-4(6aH)-one,
[19] 2-benzyl-5-phenyl-(3a,6a-cis)-1,2,3,3a-hexahydrocyclopenta[c]pyrrol-4(5H)-one;
[20] ((R,S)-5,6)-2-benzyl-6-methyl-5-phenyl-(3a,6a-cis)-1,2,3,3a-tetrahydrocyclopenta[c]pyrrol-4(1H,2H,5H)-one,
[21] ((R,S)-5,6)-2-benzyl-6-butyl-5-phenyl-(3a,6a-cis)-1,2,3,3a-hexahydrocyclopenta[c]pyrrol-4(1H,2H,5H)-one,
[22] ((R,S)-5,6)-2-benzyl-6-ethyl-5-phenyl-(3a,6a-cis)-1,2,3,3a-hexahydrocyclopenta[c]pyrrol-4(5H)-one;
[23] ((R,S)-5,6)-2-benzyl-6-isopropyl-5-phenyl-(3a,6a-cis)-1,2,3,3a-hexahydrocyclopenta[c]pyrrol-4(5H)-one;
[24] ((R,S)-5,6)-2-benzyl-5-phenyl-6-propyl-(3a,6a-cis)-1,2,3,3a-hexahydrocyclopenta[c]pyrrol-4(5H)-one;
[25] ((R,S)-5,6)-2-benzyl-6-ethyl-5-(4-fluorophenyl)-(3a,6a-cis)-1,2,3,3a-hexahydrocyclopenta[c]pyrrol-4(5H)-one;
[26] ((R,S)-5,6)-2-benzyl-5-(4-fluorophenyl)-6-propyl-(3a,6a-cis)-1,2,3,3a-hexahydrocyclopenta[c]pyrrol-4(5H)-one;
[27] ((R,S)-5,6)-2-benzyl-6-butyl-5-(4-fluorophenyl)-(3a,6a-cis)-1,2,3,3a-hexahydrocyclopenta[c]pyrrol-4(5H)-one;
[28] ((R,S)-5,6)-2-benzyl-5-(4-fluorophenyl)-6-methyl-(3a,6a-cis)-1,2,3,3a-hexahydrocyclopenta[c]pyrrol-4(5H)-one;
[29] ((R,S)-5,6)-2-benzyl-5,6-dibutyl-(3a,6a-cis)-1,2,3,3a-hexahydrocyclopenta[c]pyrrol-4(5H)-one;
[30] ((R,S)-5,6)-2-benzyl-5-butyl-6-ethyl-(3a,6a-cis)-1,2,3,3a-hexahydrocyclopenta[c]pyrrol-4(5H)-one;
[31] ((R,S)-5,6)-2-benzyl-5-butyl-6-methyl-(3a,6a-cis)-1,2,3,3a-hexahydrocyclopenta[c]pyrrol-4-(5H)-one;
[32] ((R,S)-5,6)-2-benzyl-5-butyl-6-phenyl-(3a,6a-cis)-1,2,3,3a-hexahydrocyclopenta[c]pyrrol-4(5H)-one;
[33] ((R,S)-5,6)-2-benzyl-5-(4-chlorophenyl)-6-methyl-(3a,6a-cis)-1,2,3,3a-hexahydrocyclopenta[c]pyrrol-4(5H)-one;
[34] ((R,S)-5,6)-2-benzyl-5-(4-fluorophenyl)-6-phenyl-(3a,6a-cis)-1,2,3,3a-hexahydrocyclopenta[c]pyrrol-4(5H)-one;
[35] ((R,S)-5,6)-2-benzyl-5,6-diphenyl-(3a,6a-cis)-1,2,3,3a-hexahydrocyclopenta[c]pyrrol-4(5H)-one;
[36] ((R,S)-5,6)-2-benzyl-6-(3,5-dimethylphenyl)-5-phenyl-(3a,6a-cis)-1,2,3,3a-hexahydrocyclopenta[c]pyrrol-4(5H)-one;
[37] ((R,S)-5,6)-2-benzyl-6-(4-methoxyphenyl)-5-phenyl-(3a,6a-cis)-1,2,3,3a-hexahydrocyclopenta[c]pyrrol-4(5H)-one; or
[38] ((R,S)-5,6)-2-benzyl-5-(4-chlorophenyl)-6-phenyl-(3a,6a-cis)-1,2,3,3a-hexahydrocyclopenta[c]pyrrol-4(5H)-one;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another aspect of the present invention refers to a process for obtaining substituted bicyclic tetrahydropyrrole compounds of general formula (Ia), characterized in that at least one substituted pyrroline compound of general formula (II),

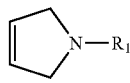
(II)

wherein $R^1$ has the meaning given above, is reacted in presence of a catalyst such as e.g. $Co_2(CO)_8$, an apolar dissolvent such as e.g. DCE (dichloroethane) and an additive such as e.g. DMSO at a reflux temperature between 20 and 100° C., preferably between 50 and 90° C., most preferably between 80 and 90° C., with a compound of general formula (III),

(III)

wherein Z represents a CH—$R^6$ group; a CH—$CHR^7R^{7a}$ group; a CH—(C=O)—$R^8$ group; a CH—$CH_2(SO_2)$—$R^9$ group; a CH—$CH_2(SO_2)$—$NR^{10}R^{10a}$ group; or a CH—(C=O)—$NR^{10}R^{10a}$ group, to give compounds of general formula (Ia),

(Ia)

wherein the bond between Y and Z is unsaturated (Y=Z) in which Y represents a CH group and Z has the meaning as defined above.

A general scheme for compounds of general formula (Ia) with Y and Z forming an unsaturated bond (Y=Z) is given below in scheme (I):

SCHEME (I)

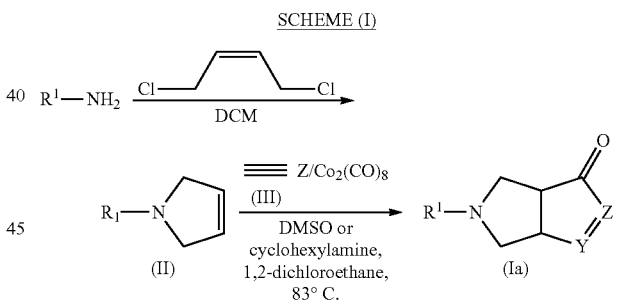

The synthesis of 1-substituted-3-pyrrolines of general formula (II) is well known by those skilled in the art and is described in e.g. JP2001278857, JP2001270862, Synthetic Communications 1990, 20(2), 227-230, Synthetic Communications 2004, 34(23), 4421 or JP2005120067.

Compounds of general formula (I) with Y and Z forming a saturated (Y—Z) bond are obtained by performing a 1,4-addition reaction with a compound of general formula (Ia),

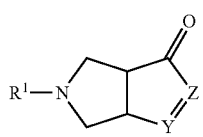
(Ia)

wherein $R^1$ has the meaning as described above, Z represents a CH—$R^6$ group; a CH—$CHR^7R^{7a}$ group; a CH—(C=O)—$R^8$ group; a CH—$CH_2(SO_2)$—$R^9$ group; a CH—$CH_2$ $(SO_2)$—$NR^{10}R^{10a}$ group; or a CH—(C=O)—$NR^{10}R^{10a}$ group and Y represents a CH group, to give a compound of general formula (Ib),

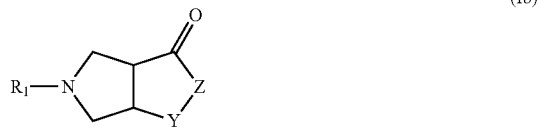

(Ib)

wherein $R^1$ has the meaning as defined above, Y and Z, as defined above, form a saturated (Y—Z) bond, and Y represents a $CH_2$ group; a C—$R^{11}R^{12}$ group; a CH—(C=O)—$R^{16}$ group; a CH—$(SO_2)$—$R^{17}$ group; CH—$(SO_2)$—$NR^{18}R^{18a}$ group; or a CH—(C=O)—$NR^{18}R^{18a}$ group.

The performance of said 1,4-addition reaction is well known by those skilled in the art and is preferably done in the presence of a catalyst such as Copper iodide or Rh and an apolar substrate such as e.g. $Et_2O$ or dioxane. The reactants in this 1,4-addition may be metallic or non-metallic. Preferably, the reactants are metallic.

Preferred examples of metallic reactants are Y—Li and Y—$Mg_X$, wherein Y represents a $CH_2$ group; a C—$R^{11}R^{12}$ group; a CH—(C=O)—$R^{16}$ group; a CH—$(SO_2)$—$R^{17}$ group; CH—$(SO_2)$—$NR^{18}R^{18a}$ group; or a CH—(C=O)—$NR^{18}R^{18a}$ group; and x refers to the valency of Mg, depending on the ligand Y. Other preferred examples of metalloid reactants are Y—$B(OR)_2$ (boronic acid or boronates), wherein Y represents an aryl or heteroaryl group.

A general scheme for compounds of general formula (Ib) with Y and Z forming a saturated bond (Y—Z) is given below in scheme (II):

SCHEME (II)

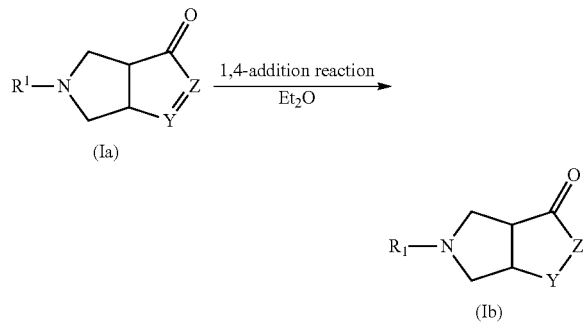

During the processes described above the protection of sensitive groups or of reagents may be necessary and/or desirable. The introduction of conventional protective groups as well as their removal may be performed by methods well-known to those skilled in the art.

If the compounds of general formula (I) themselves are obtained in form of a mixture of stereoisomers, particularly enantiomers or diastereomers, said mixtures may be separated by standard procedures known to those skilled in the art, e.g. chromatographic methods or fractionalized crystallization with chiral reagents. If there are chiral centers the compounds may be prepared in racemic form, or individual enantiomers may be prepared either by enantiospecific synthesis or by resolution.

Solvates, preferably hydrates, of the compounds of general formula (I), of corresponding stereoisomers, or of corresponding salts thereof may also be obtained by standard procedures known to those skilled in the art.

The purification and isolation of the inventive compounds of general formula (I), of a corresponding stereoisomer, or salt, or solvate or any intermediate thereof may, if required, be carried out by conventional methods known to those skilled in the art, e.g. chromatographic methods or recrystallization.

It has been found that the compounds of general formula (I) and given below, stereoisomers thereof, corresponding salts and corresponding solvates have high affinity to sigma receptors, i.e. they are selective ligands for the sigma receptor and act as modulators, e.g. antagonists, inverse agonists or agonists, on these receptors.

The compounds of general formula (I) given below, their stereoisomers, corresponding salts thereof and corresponding solvates are toxicologically acceptable and are therefore suitable as pharmaceutical active substances for the preparation of medicaments.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the Invention encompasses all such forms.

Another aspect of the present invention relates to a medicament comprising at least one compound of general formula (I), optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof; or a prodrug thereof.

In an alternative embodiment of the present invention, the medicament comprises at least one compound of general formula (I), said compound being optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another aspect of the invention is a medicament comprising at least one combination of compounds according to the invention and optionally one or more pharmaceutically acceptable excipients.

In an embodiment according to the invention the medicament is for the prophylaxis and/or treatment of Alzheimer's disease.

In an embodiment according to the invention the medicament is for the prophylaxis and/or treatment of one or more disorders selected from the group consisting of diarrhea, lipoprotein disorders, migraine, obesity, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer or psychotic conditions, in particular depression, anxiety, psychosis or schizophrenia; inflammation, or autoimmune diseases.

In an embodiment according to the invention the medicament is for the prophylaxis and/or treatment of one or more disorders selected from the group consisting of elevated triglyceride levels, chylomicronemia, dysbetalipoproteinemia, hyperlipoproteinemia, hyperlipidemia, mixed hyperlipidemia, hypercholesterolemia, lipoprotein disorders, hypertriglyceridemia, sporadic hypertriglyceridemia, inherited hypertriglyceridemia and/or dysbetalipoproteinemia.

In another embodiment according to the invention the medicament is for the prophylaxis and/or treatment of one or more disorders selected from the group consisting of pain, preferably neuropathic pain, inflammatory pain or other pain conditions involving allodynia and/or hyperalgesia.

Said medicament may also comprise any combination of one or more of the compounds of general formula (I) given above, stereoisomers thereof, physiologically acceptable salts thereof or physiologically acceptable solvates thereof.

Another aspect of the present invention is the use of at least one compound of general formula (I) given above as suitable active substances, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, and optionally one or more pharmaceutically acceptable excipients, for the preparation of a medicament for the modulation of sigma receptors, preferably for the prophylaxis and/or treatment of Alzheimer's disease.

The medicament according to the present invention may be in any form suitable for the application to humans and/or animals, preferably humans including infants, children and adults and can be produced by standard procedures known to those skilled in the art. The composition of the medicament may vary depending on the route of administration.

The medicament of the present invention may for example be administered parentally in combination with conventional injectable liquid carriers, such as water or suitable alcohols. Conventional pharmaceutical excipients for injection, such as stabilizing agents, solubilizing agents, and buffers, may be included in such injectable compositions. These medicaments may for example be injected intramuscularly, intraperitoneally, or intravenously.

Solid oral compositions (which are preferred as are liquid ones) may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to the methods well known in normal pharmaceutical practice, in particular with an enteric coating.

The mentioned formulations will be prepared using standard methods such as those described or referred to in the Spanish and US Pharmacopeias and similar reference texts.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered forms suitable for reconstitution with water or other suitable liquid medium before use, for immediate or retarded release.

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

Anther aspect of the present invention refers to a method for the prophylaxis and/or treatment of Alzheimer's disease, the method comprising administering to the subject at least one compound of general formula (I) as described above and optionally at least one further active substance and/or optionally at least one auxiliary substance to the subject.

Another aspect of the present invention refers to a method for the prophylaxis and/or treatment of diarrhea, lipoprotein disorders, migraine, obesity, elevated triglyceride levels, chylomicronemia, dysbetalipoproteinemia, hyperlipoproteinemia, hyperlipidemia, mixed hyperlipidemia, hypercholesterolemia, lipoprotein disorders, hypertriglyceridemia, sporadic hypertriglyceridemia, inherited hypertriglyceridemia and dysbetalipoproteinemia, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer or psychotic conditions, in particular depression, anxiety or schizophrenia; inflammation, or autoimmune diseases, the method comprising administering to the subject at least one compound of general formula (I) as described above and optionally at least one further active substance and/or optionally at least one auxiliary substance to the subject.

A preferred embodiment of the present invention refers to a method for the prophylaxis and/or treatment of elevated triglyceride levels, chylomicronemia, dysbetalipoproteinemia, hyperlipoproteinemia, hyperlipidemia, mixed hyperlipidemia, hypercholesterolemia, lipoprotein disorders, hypertriglyceridemia, sporadic 1 hypertriglyceridemia, inherited hypertriglyceridemia and/or dysbetalipoproteinemia.

The present invention is illustrated below with the aid of examples. These illustrations are given solely by way of example and do not limit the general spirit of the present invention.

EXAMPLES

Synthesis of Intermediates

Example 0

1-Benzyl-3-pyrroline

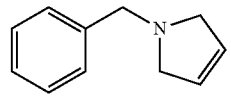 [SMILES: C1=CCN(Cc2ccccc2)C1]

Was synthesized according to published methods with slight modifications: a) EP0985664, b) Synthetic Communications 13(13), 1117-1123 (1983).

To a solution of cis-1,4-dichloro-2-butene (0.76 g, 5.77 mmol) in anhydrous dichloromethane (4 ml) cooled at 5° C., benzylamine (3.75 g, 34.66 mol) was added dropwise. The mixture was stirred at 5° C. for 10 min and after at r.t. 24 hours. The white solid was filtered and washed with dichloromethane. The filtrated was cooled at 0° C. and HCl 37% (0.6 ml) was added. The resulting white solid was filtered and washed with dichloromethane. The filtrate was concentrated to give an orange oil that was purified by flash chromatography: silica gel, hexane:ethyl acetate (1:1) to afforded the product (0.76 g, 82%) as yellow oil.

$^1$H NMR (400 MHz, CDCl3): δ (ppm) 7.38-7.21 (m, 5H), 5.78 (s, 2H), 3.80 (s, 3H), 3.81 (s, 2H), 3.48 (s, 4H). $^{13}$C NMR (75 MHz, CDCl$_3$) δ (ppm) 139.67, 128.69, 128.34, 127.78, 126.96, 60.40, 59.70.

Example 0-A 1-(4-methoxybenzyl)-3-pyrroline

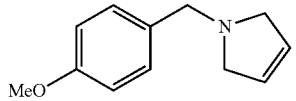 [SMILES: COc1ccc(CN2CC=CC2)cc1]

To a solution of 1,4-dimethylsulphonyl-2-butene (2.15 g, 11.64 mmol) in dichloromethane (40 ml), 4-methoxybenzylamine (6 ml, 44.24 mmol) was added dropwise and the solution was stirred 20 hours at r.t. The solid was filtrated and the filtrate was washed with water (2×30 ml), dried over Na$_2$SO$_4$, filtered and concentrated. The crude was purified by flash chromatography: silica gel, gradient hexane:ethyl acetate 3:1 to 1:1. to afforded the product (1.4 g, 63%) as yellow oil.

$^1$H NMR (400 MHz, CDCl3): δ (ppm) 7.29 (d, J=8.5 Hz, 2H), 6.87 (d, J=8.5 Hz, 2H), 5.79 (s, 2H), 3.80 (s, 3H), 3.76 (s, 2H), 3.48 (s, 4H). $^{13}$C NMR (75 MHz, CDCl$_3$) δ(ppm) 158.83, 131.85, 129.83, 128.03, 114.31, 59.69, 59.56, 55.23.

Example 0-B 1-((S)-alpha-methylbenzyl)-3-pyrroline

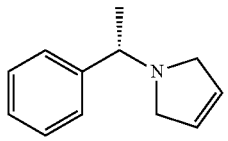

Was synthesized according to published methods with slight modifications: a) EP0985664, b) Synthetic Communications 34(23), 4421-4430 (2004).

To a solution of 1,4-dimethylsulphonyl-2-butene (0.52 g, 2.86 mmol) in dichloromethane (10 ml), (S)-alpha-methylbenzylamine (1.31 g, 10.87 mmol) was added and the solution was stirred 20 hours at r.t. The solid obtained was filtrated and the filtrate was washed with water (2×30 ml), dried over Na$_2$SO$_4$, filtered and concentrated. The crude was purified by flash chromatography: silica gel, gradient hexane to hexane:ethyl acetate 1:1 to afforded the product (0.45 g, 90%) as yellow oil.

$^1$H NMR (400 MHz, CDCl3): δ (ppm) 7.42-7.25 (m, 5H), 5.80 (s, 2H), 3.53 (q, J=6.5 Hz, 1H), 3.44 (m, 2H), 3.36 (m, 2H), 1.44 (d, J=6.5 Hz, 3H). $^{13}$C NMR (75 MHz, CDCl$_3$) δ (ppm) 145.90, 128.47, 127.67, 127.28, 127.07, 65.30, 58.55, 23.50.

Example 0-C 1-(Benzhydryl)-3-pyrroline

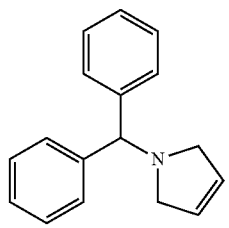 [SMILES: C1=CCN(C(c2ccccc2)c2ccccc2)C1]

To a solution of aminodiphenylmethane (9.70 g, 51.46 mmol) in dichloromethane (6 ml) was added cis-1,4-dichloro-2-butene (1.18 g, 9.02 mmol). The mixture was stirred at r.t. 20 hours. The white solid was filtered and washed with dichloromethane. The filtrated was cooled at 0° C. and HCl 37% (2.5 ml) was added carefully and the suspension was stirred overnight. The resulting white solid was filtered and washed with dichloromethane and the filtrated was washed with saturated solution of NaHCO$_3$, water, dried over Na$_2$SO$_4$, filtered and concentrated. The crude was purified by flash chromatography: silica gel, gradient dichloromethane to dichloromethane:methanol 4% to afforded the product (0.90 g, 43%) as white solid. M.p. 90-91° C.

$^1$H NMR (400 MHz, CDCl3): δ (ppm) 7.54 (d, J=7 Hz, 4H), 7.31 (t, J=7 Hz, 4H), 7.19 (t, J=7 Hz, 2H), 5.81 (s, 2H), 4.62 (s, 1H), 3.43 (s, 4H). $^{13}$C NMR (75 MHz, CDCl$_3$) δ(ppm) 144.12, 128.56, 127.62, 127.50, 127.00, 76.00, 59.37.

Example 0-D 1-(4-fluorobenzyl)-3-pyrroline

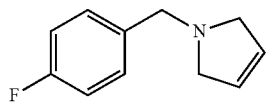 [SMILES: Fc1ccc(CN2CC=CC2)cc1]

To a solution of cis-1,4-dichloro-2-butene (0.50 g, 3.8 mmol) in anhydrous dichloromethane (4 ml) cooled at 0° C., 4-fluorobenzylamine (2.94 g, 22.8 mol) was added dropwise. The mixture was stirred at 0° C. for 10 min and then at r.t. 24 hours. The white solid was filtered and washed with dichloromethane. The filtrated was cooled at 0° C. and HCl 10% was added until slightly acid pH. The resulting white solid was filtered and washed with dichloromethane. The filtrate was concentrated and the residue was purified by flash chromatography: silica gel, hexane:ethyl acetate (1:1) to afforded the product (353 mg, 52%) as yellow oil.

$^1$H NMR (400 MHz, CDCl3): δ (ppm) 7.31 (m, 2H), 6.99 (m, 2H), 5.78 (s, 2H), 3.77 (s, 2H), 3.46 (s, 4H). $^{13}$C NMR (75 MHz, CDCl$_3$) δ (ppm) 161.91 (d, J$_{CF}$=243 Hz), 135.41, 130.14 (d, J$_{CF}$=8 Hz), 127.78, 115.05 (d, J$_{CF}$=21 Hz), 59.59, 59.52. MS (ES+) m/z: 178.1 (M+H$^+$).

General Procedure for the synthesis of Pauson-Khand adducts. To a solution of the acetylene (1.1 eq) in 1,2-dichloroethane, was added Co₂(CO)₈ (1.1 eq) and the mixture was stirred 2 hours at room temperature. A solution of the pyrroline (1 eq) in 1,2-dichloroethane and the additive (dimethylsulfoxide or cyclohexylamine) (3.5 eq) were added and the mixture was heated at 83° C. for 20 hours.

The reaction mixture was filtered through celite and washed with CH₂Cl₂. The filtrate was concentrated and the crude was purified by flash chromatography.

Example 1

2-benzyl-5-phenyl-(3a,6a-cis)-1,2,3,3a-tetrahydrocyclopenta[c]pyrrol-4(6aH)-one

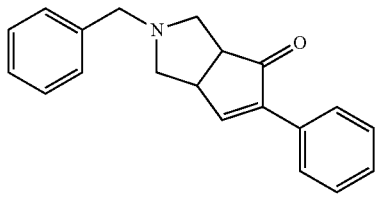 [SMILES: O=C1C(c2ccccc2)=CC2CN(Cc3ccccc3)CC12]

From phenylacetylene (5.0 g, 48.3 mmol), Co₂(CO)₈ (16.5 g, 48.3 mmol), 1-benzyl-3-pyrroline (7.0 g, 43.9 mmol), dimethylsulfoxide (12.0 g, 153.8 mmol) and 1,2-dichloroethane (200 ml). Purification: silica gel, gradient dichloromethane to dichloromethane:methanol 1%, afforded the product (5.9 g, 46%) as yellow oil.

¹H NMR (400 MHz, CDCl₃): δ (ppm) 7.72 (m, 2H), 7.65 (d, J=3 Hz, 1H), 7.40-7.18 (m, 8H), 3.49-3.63 (AB system, 2H), 3.36 (m, 1H), 3.19 (d, J=9 Hz, 1H), 2.94 (m, 1H), 2.83 (d, J=9 Hz, 1H), 2.43 (t, J=9 Hz, 1H), 2.37 (t, J=9 Hz, 1H). ¹³C NMR (75 MHz, CDCl₃) δ (ppm) 208.94, 159.74, 143.79, 138.30, 131.47, 128.45, 128.38, 128.34, 128.18, 58.91, 56.79, 55.89, 50.24, 42.58. MS (EI+) m/z: 289.14 (M⁺).

Example 2

5-phenyl-2-((S)-1-phenylethyl)-(3a,6a-cis)-1,2,3,3a-tetrahydrocyclopenta[c]pyrrol-4(6aH)-one

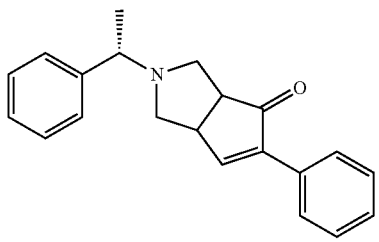 [SMILES: C[C@@H](c1ccccc1)N1CC2C=C(c3ccccc3)C(=O)C2C1]

From phenylacetylene (37 mg, 0.35 mmol), Co₂(CO)₈ (121 mg, 0.35 mmol), 1-(S)-alpha-methyl-benzyl-3-pyrroline (56 mg, 0.32 mmol), dimethylsulfoxide (72 μl, 1.01 mmol) and 1,2-dichloroethane (2 ml). Purification: silica gel, gradient: dichloromethane to dichloromethane:methanol 1%, afforded the product (70 mg, 71%) as yellow oil, as mixture of two diastereomers (1.1).

¹H NMR (400 MHz, CDCl₃): δ (ppm) 7.78-7.71 (m, 4H), 7.70 (d, J=3 Hz, 1H), 7.59 (d, J=3 Hz, 1H), 7.44-7.16 (m, 16H), 3.41 (d, J=9 Hz), 3.38 (m, 1H), 3.28 (m, 1H), 3.21 (q, J=6.5 Hz, 1H), 3.18 (q, J=6.5 Hz, 1H), 3.01 (d, J=9 Hz, 1H), 2.96 (m, 1H), 2.94 (d, J=9 Hz, 1H), 2.88 (m, 1H), 2.63 (d, J=9 Hz, 1H), 2.42 (m, 2H), 2.31 (t, J=9 Hz, 1H), 2.21 (t, J=9 Hz, 1H), 1.30 (d, J=6.5 Hz, 3H), 1.29 (d, J=6.5 Hz, 3H). ¹³C NMR (75 MHz, CDCl₃) δ (ppm) 209.33, 208.88, 160.05, 159.82, 143.72, 143.60, 131.51, 128.89, 128.50, 128.37, 128.31, 128.27, 127.93, 127.92, 127.16, 127.14, 126.90, 126.88, 126.84, 126.20, 64.31, 64.13, 55.53, 55.28, 55.16, 54.44, 50.11, 50.03, 42.39, 42.27, 41.74, 23.07, 22.65. MS (EI+) m/z: 304.15 (M+H⁺).

Example 3

2-(4-methoxybenzyl)-5-phenyl-(3a,6a-cis)-1,2,3,3a-tetrahydrocyclopenta[c]pyrrol-4(6aH)-one

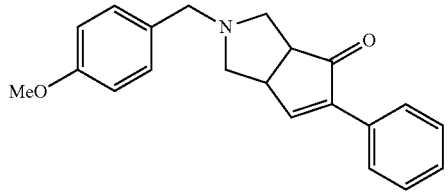 [SMILES: COc1ccc(CN2CC3C=C(c4ccccc4)C(=O)C3C2)cc1]

From phenylacetylene (930 mg, 8.93 mmol), Co₂(CO)₈ (3.0 g, 8.93 mmol), 1-(4-methoxy)-benzyl-3-pyrroline (1.3 g, 6.86 mmol), dimethylsulphoxide (2.1 g, 27.47 mmol) and 1,2-dichloroethane (30 ml). Reaction time 48 hours. Purification: silica gel, grad. dichloromethane to dichloromethane:methanol 1%, afforded the product (985 mg, 45%) as yellow oil.

¹H NMR (400 MHz, CDCl₃): δ (ppm) 7.75-7.71 (m, 2H), 7.66 (d, J=3 Hz, 1H), 7.42-7.31 (m, 3H), 7.12 (d, J=8.7 Hz, 2H), 6.80 (d, J=8.7 Hz, 2H), 3.78 (s, 3H), 3.57-3.44 (AB system, 2H), 3.37 (m, 1H), 3.17 (d, J=9 Hz, 1H), 2.95 (m, 1H), 2.82 (d, J=9 Hz, 1H), 2.42 (t, J=9 Hz, 1H), 2.36 (t, J=9 Hz, 1H). ¹³C NMR (75 MHz, CDCl₃) δ (ppm) 209.07, 159.87, 158.53, 143.70, 131.46, 130.42, 129.58, 128.36, 127.14, 113.53, 58.25, 56.68, 55.77, 55.16, 50.22, 42.56. MS (EI+) m/z: 319.15 (M⁺).

Example 4

2-benzyl-5-(4-fluorophenyl)-(3a,6a-cis)-1,2,3,3a-tetrahydrocyclopenta[c]pyrrol-4(6aH)-one

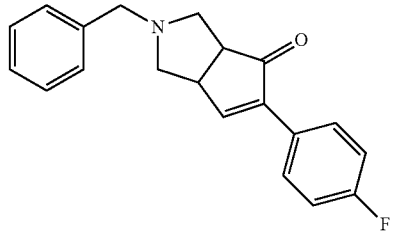 [SMILES: O=C1C(c2ccc(F)cc2)=CC2CN(Cc3ccccc3)CC12]

From 1-ethynyl-4-fluorobenzene (151 mg, 1.25 mmol), Co₂(CO)₈ (472 mg, 1.38 mmol), 1-benzyl-3-pyrroline (200 mg, 1.25 mmol), cyclohexylamine (436 mg, 4.39 mmol) and 1,2-dichloroethane (20 ml). Purification: silica gel, hexane:ethyl acetate (1:1), afforded the product (126 mg, 33%) as yellow oil.

¹H NMR (400 MHz, CDCl₃): δ (ppm) 7.75-7.71 (m, 2H), 7.63 (d, J=3 Hz, 1H), 7.29-7.24 (m, 3H), 7.21 (m, 2H), 7.07 (m, 2H), 3.63-3.50 (AB system, 2H), 3.38 (m, 1H), 3.19 (d, J=9 Hz, 1H), 2.94 (t, J=9 Hz, 1H), 2.84 (d, J=9 Hz, 1H), 2.43 (t, J=9 Hz, 1H), 2.37 (t, J=9 Hz, 1H). ¹³C NMR (75 MHz, CDCl₃) δ (ppm) 208.92, 164.04, 159.37, 142.72, 138.28, 128.91, 128.45, 128.24, 128.19, 126.94, 115.41, 115.19, 58.91, 56.80, 55.87, 50.18, 42.53. HRMS (ES+) m/z: calcd for C₂₀H₁₉NOF (M+H⁺): 308.1451; found: 308.1446.

Example 5

2-benzyl-5-(4-ethylphenyl)-(3a,6a-cis)-1,2,3,3a-tetrahydrocyclopenta[c]pyrrol-4(6aH)-one

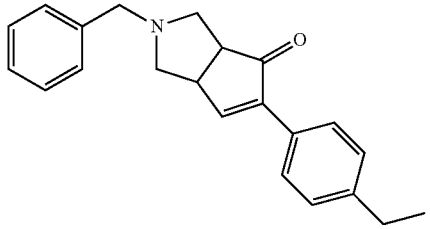 [SMILES: CCc1ccc(C2=CC3CN(Cc4ccccc4)CC3C2=O)cc1]

From 1-ethyl-4-ethynylbenzene (168 mg, 1.25 mmol), Co₂(CO)₈ (472 mg, 1.38 mmol), 1-benzyl-3-pyrroline (200 mg, 1.25 mmol), cyclohexylamine (436 mg, 4.39 mmol) and 1,2-dichloroethane (20 ml). Purification: silica gel, hexane:ethyl acetate (1:1), to afforded the product (40 mg, 10%) as yellow oil.

¹H NMR (400 MHz, CDCl₃): δ (ppm) 7.65 (m, 2H), 7.61 (d, J=3 Hz, 1H), 7.29-7.17 (m, 7H), 3.64-3.49 (AB system, 2H), 3.36 (m, 1H), 3.19 (d, J=9 Hz, 1H), 2.94 (m, 1H), 2.83 (d, J=9 Hz, 1H), 2.66 (q, J=8.5 Hz, 2H), 2.44 (t, J=9 Hz, 1H), 2.37 (t, J=9 Hz, 1H), 1.24 (t, J=8.5 Hz, 3H). ¹³C NMR (75 MHz, CDCl₃) δ (ppm) 209.17, 159.03, 144.69, 143.73, 138.49, 128.90, 128.45, 128.19, 127.90, 127.16, 126.89, 58.98, 56.89, 56.03, 50.27, 42.59, 28.70, 15.54. HRMS (ES+) m/z: calcd for C₂₂H₂₄NO (M+H⁺): 318.1858; found: 318.1854.

Example 6

2-benzyl-5-(2-chlorophenyl)-(3a,6a-cis)-1,2,3,3a-tetrahydrocyclopenta[c]pyrrol-4(6aH)-one

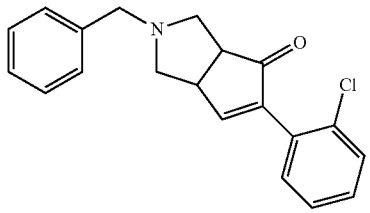 [SMILES: O=C1C(c2ccccc2Cl)=CC2CN(Cc3ccccc3)CC12]

From 1-chloro-2-ethynylbenzene (171 mg, 1.25 mmol), Co₂(CO)₈ (472 mg, 1.38 mmol), 1-benzyl-3-pyrroline (200 mg, 1.25 mmol), dimethylsulphoxide (343 mg, 4.39 mmol) and 1,2-dichloroethane (20 ml). Purification: silica gel, hexane:ethyl acetate (1:1), afforded the product (128 mg, 32%) as yellow oil.

¹H NMR (400 MHz, CDCl3): δ (ppm) 7.68 (d, J=3 Hz, 1H), 7.45-7.18 (m, 9H), 3.68-3.44 (AB system, 2H), 3.46 (m, 1H), 3.20 (d, J=9 Hz, 1H), 2.94 (m, 1H), 2.88 (d, J=9 Hz, 1H), 2.46 (t, J=9 Hz, 1H), 2.38 (t, J=9 Hz, 1H). ¹³C NMR (75 MHz, CDCl₃) δ(ppm) 208.26, 163.70, 143.22, 138.65, 133.05, 130.80, 129.80, 129.25, 128.29, 128.18, 126.89, 126.49, 58.73, 56.95, 55.66, 49.17, 43.37. HRMS (ES+) m/z: calcd for C₂₈H₁₉NOCl (M+H⁺): 324.1155; found: 324.1140.

Example 7

2-benzyl-5-(4-chlorophenyl)-(3a,6a-cis)-1,2,3,3a-tetrahydrocyclopenta[c]pyrrol-4(6aH)-one

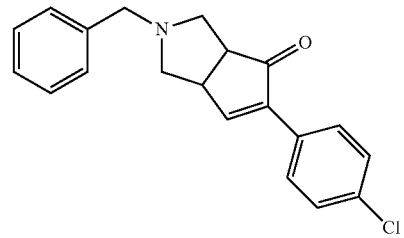 [SMILES: O=C1C(c2ccc(Cl)cc2)=CC2CN(Cc3ccccc3)CC12]

From 1-chloro-4-ethynylbenzene (171 mg, 1.25 mmol), Co₂(CO)₈ (472 mg, 1.38 mmol), 1-benzyl-3-pyrroline (200 mg, 1.25 mmol), dimethylsulphoxide (343 mg, 4.39 mmol), and 1,2-dichloroethane (20 ml) Purification: silica gel, hexane:ethyl acetate (1:1), afforded the product (148 mg, 36%) as yellow oil.

¹H NMR (400 MHz, CDCl₃): δ (ppm) 7.74 (m, 1H), 7.69 (d, J=3 Hz, 1H), 7.63 (m, 1H), 7.32-7.19 (m, 7H), 3.63-3.50 (AB system, 2H), 3.38 (m, 1H), 3.19 (d, J=9 Hz, 1H), 2.95 (m, 1H), 2.85 (d, J=9 Hz, 1H), 2.43 (t, J=9 Hz, 1H), 2.38 (t, J=9 Hz, 1H). ¹³C NMR (75 MHz, CDCl₃) δ (ppm) 208.53, 160.63, 142.63, 138.30, 134.36, 133.21, 129.65, 128.48, 128.26, 127.24, 127.00, 125.33, 58.94, 56.87, 55.84, 50.27, 42.69. HRMS (ES+) m/z: calcd for C₂₀H₁₉NOCl (M+H⁺): 324.1155; found: 324.1144.

Example 8

2-benzyl-5-(3-chlorophenyl)-(3a,6a-cis)-1,2,3,3a-tetrahydrocyclopenta[c]pyrrol-4(6aH)-one

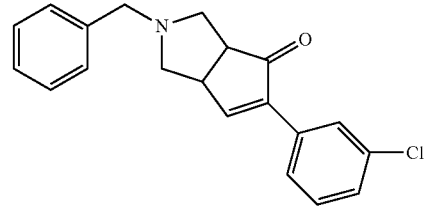 [SMILES: O=C1C(c2cccc(Cl)c2)=CC2CN(Cc3ccccc3)CC12]

From 3-chloro-1-ethynylbenzene (171 mg, 1.25 mmol), Co₂(CO)₈ (472 mg, 1.38 mmol), 1-benzyl-3-pyrroline (200 mg, 1.25 mmol), dimethylsulphoxide (343 mg, 4.39 mmol), and 1,2-dichloroethane (20 ml). Purification: silica gel, hexane:ethyl acetate (1:1), afforded the product (143 mg, 35%) as yellow oil.

¹H NMR (400 MHz, CDCl₃): δ (ppm) 7.69 (m, 2H), 7.67 (d, J=3 Hz, 1H), 7.35 (m, 2H), 7.26-7.18 (m, 5H), 3.64-3.50 (AB system, 2H), 3.37 (m, 1H), 3.19 (d, J=9 Hz, 1H), 2.94 (m, 1H), 2.85 (d, J=9 Hz, 1H), 2.44 (t, J=9 Hz, 1H), 2.38 (t, J=9

Hz, 1H). $^{13}$C NMR (75 MHz, CDCl$_3$) δ (ppm) 208.78, 159.93, 142.67, 138.31, 134.36, 129.89, 128.59, 128.47, 128.22, 126.97, 58.92, 56.85, 55.86, 50.24, 42.64. HRMS (ES+) m/z: calcd for C$_{20}$H$_{19}$NOCl (M+H$^+$): 324.1155; found: 324.1150.

Example 9

2-benzyl-5-(4-methoxyphenyl)-(3a,6a-cis)-1,2,3,3a-tetrahydrocyclopenta[c]pyrrol-4(6aH)-one

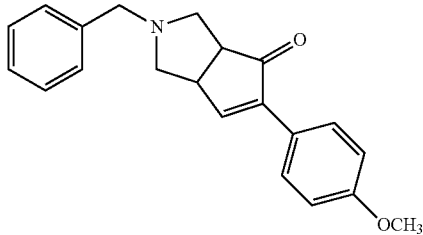 [SMILES: COc1ccc(C2=CC3CN(Cc4ccccc4)CC3C2=O)cc1]

From 1-ethynyl-4-methoxybenzene (166 mg, 1.25 mmol), Co$_2$(CO)$_{13}$ (472 mg, 1.38 mmol), 1-benzyl-3-pyrroline (200 mg, 1.25 mmol), dimethylsulphoxide (343 mg, 4.39 mmol), and 1,2-dichloroethane (20 ml). Purification: silica gel, hexane:ethyl acetate (1:1), afforded the product (166 mg, 41%) as yellow oil.

$^1$H NMR (400 MHz, CDCl$_3$): δ (ppm) 7.71 (d, J=8.5 Hz, 2H), 7.58 (d, J=3 Hz, 1H), 7.29-7.19 (m, 5H), 6.92 (d, J=8.5 Hz, 2H), 3.83 (s, 3H), 3.64-3.50 (AB system, 2H), 3.36 (m, 1H), 3.18 (d, J=9 Hz, 1H), 2.94 (m, 1H), 2.83 (d, J=9 Hz, 1H), 2.42 (t, J=9 Hz, 1H), 2.36 (t, J=9 Hz, 1H). $^{13}$C NMR (75 MHz, CDCl$_3$) δ (ppm) 209.35, 159.78, 157.98, 143.09, 138.43, 128.47, 128.43, 128.19, 126.90, 124.12, 113.81, 59.00, 56.84, 56.08, 55.28, 50.26, 42.49. HRMS (ES+) m/z: calcd for C$_{21}$H$_{22}$NO$_2$ (M+H$^+$): 320.1651; found: 320.1649.

Example 10

2-benzyl-5-(biphenyl-4-yl)-(3a,6a-cis)-1,2,3,3a-tetrahydrocyclopenta[c]pyrrol-4(6aH)-one

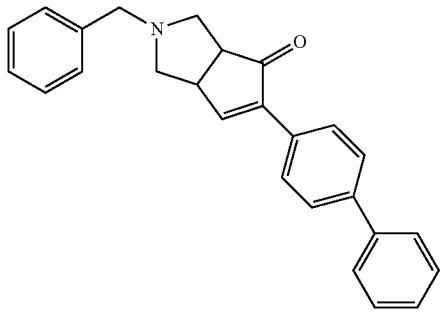 [SMILES: O=C1C(c2ccc(-c3ccccc3)cc2)=CC2CN(Cc3ccccc3)CC12]

From 4-ethynyl-1,1'-biphenyl (246 mg, 1.38 mmol), Co$_2$(CO)$_8$ (472 mg, 1.38 mmol), 1-benzyl-3-pyrroline (200 mg, 1.25 mmol), dimethylsulphoxide (343 mg, 4.39 mmol), and 1,2-dichloroethane (20 ml). Purification: silica gel, hexane:ethyl acetate (2:1), afforded the product (163 mg, 35%) as yellow oil.

$^1$H NMR (400 MHz, CDCl3): δ (ppm) 7.82 (m, 2H), 7.71 (d, J=3 Hz, 1H), 7.64-7.59 (m, 4H), 7.47-7.20 (m, 8H), 3.65-3.50 (AB system, 2H), 3.39 (m, 1H), 3.21 (d, J=9 Hz, 1H), 2.97 (m, 1H), 2.86 (d, J=9 Hz, 1H), 2.45 (t, J=9 Hz, 1H), 2.39 (t, J=9 Hz, 1H). $^{13}$C NMR (75 MHz, CDCl$_3$) δ (ppm) 209.10, 159.65, 143.40, 141.21, 138.43, 131.80, 130.46, 128.78, 128.46, 128.22, 127.58, 127.41, 127.10, 127.05, 126.94, 58.98, 56.91, 50.32, 42.70. HRMS (ES+) m/z calcd for C$_{26}$H$_{24}$NO (M+H$^+$): 366.1858; found: 366.1848.

Example 11

2-benzyl-5-(4-tert-butylcarbamatephenyl)-(3a,6a-cis)-1,2,3,3a-tetrahydrocyclopenta[c]pyrrol-4(6aH)-one

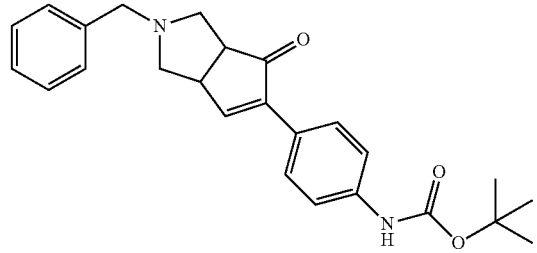 [SMILES: CC(C)(C)OC(=O)Nc1ccc(C2=CC3CN(Cc4ccccc4)CC3C2=O)cc1]

From 4-ethynyl-Boc-aniline (202 mg, 0.93 mmol), Co$_2$(CO)$_8$ (319 mg, 0.93 mmol), 1-benzyl-3-pyrroline (135 mg, 0.84 mmol), dimethylsulphoxide (232 mg, 2.96 mmol) and 1,2-dichloroethane (14 ml). Purification: silica gel, hexane:ethyl acetate (10:1), afforded the product (50 mg, 15%) as yellow oil.

$^1$H NMR (400 MHz, CDCl$_3$): δ (ppm) 7.62 (m, 2H), 7.53 (d, J=3 Hz, 1H), 7.32-7.10 (m, 7H), 3.55-3.43 (AB system, 2H), 3.27 (m, 1H), 3.10 (d, J=9 Hz, 1H), 2.85 (m, 1H), 2.78 (d, J=9 Hz, 1H), 2.35 (t, J=9 Hz, 1H), 2.29 (t, J=9 Hz, 1H), 1.45 (s, 9H). $^{13}$C NMR (75 MHz, CDCl$_3$) δ (ppm) 215.15, 158.64, 152.60, 143.05, 138.63, 138.41, 128.55, 128.27, 127.86, 126.95, 126.64, 126.21, 118.14, 81.20, 59.08, 56.81, 56.03, 50.34, 42.56, 28.38. MS (ES+) m/z: 405.21 (M+H$^+$).

Example 12

2-benzyl-5-butyl-(3a,6a-cis)-1,2,3,3a-tetrahydrocyclopenta[c]pyrrol-4(6aH)-one

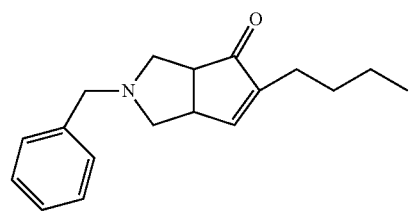 [SMILES: CCCCC1=CC2CN(Cc3ccccc3)CC2C1=O]

From 1-hexyne (26 mg, 0.31 mmol), Co$_2$(CO)$_3$ (118 mg, 0.34 mmol), 1-benzyl-3-pyrroline (50 mg, 0.31 mmol), dimethylsulphoxide (86 mg, 1.1 mmol) and 1,2-dichloroethane (2 ml). Purification: silica gel, hexane:ethyl acetate (1:1), afforded the product (45 mg, 53%) as yellow oil.

$^1$H NMR (400 MHz, CDCl$_3$): δ (ppm) 7.30-7.16 (m, 5H), 7.11 (m, 1H), 3.61-3.46 (AB system, 2H), 3.23 (m, 1H), 3.07 (d, J=9 Hz, 1H), 2.75 (m, 1H), 2.71 (d, J=9 Hz, 1H), 2.35 (t, J=9 Hz, 1H), 2.28 (t, J=9 Hz, 1H), 2.19 (m, 2H), 1.50 (m, 2H), 1.36 (m, 2H), 0.92 (t, J=7 Hz, 3H). $^{13}$C NMR (75 MHz, CDCl$_3$) δ (ppm) 211.29, 158.48, 146.98, 138.62, 128.38, 128.13, 126.84, 58.91, 56.67, 55.98, 49.19, 43.03, 29.83, 24.42, 22.28, 13.83. MS (ES+) m/z: 270.2 (M+H$^+$).

Example 13

2-benzhydryl-5-phenyl-(3a,6a-cis)-1,2,3,3a-tetrahydrocyclopenta[c]pyrrol-4(6aH)-one

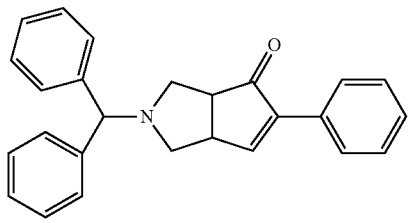 [SMILES: O=C1C(c2ccccc2)=CC2CN(C(c3ccccc3)c3ccccc3)CC12]

From phenylacetylene (22 mg, 0.21 mmol), Co$_2$(CO)$_8$ (90 mg, 0.26 mmol), 1-benzyl-3-pyrroline (50 mg, 0.31 mmol), dimethylsulphoxide (58 mg, 1.1 mmol) and 1,2-dichloroethane (2 ml). Purification: silica gel, hexane:ethyl acetate (10:1), afforded the product (16 mg, 21%) as yellow oil.

$^1$H NMR (400 MHz, CDCl$_3$): δ (ppm) 7.77 (m, 2H), 7.67 (d, J=3 Hz, 1H), 7.55-7.35 (m, 4H), 7.32-7.11 (m, 9H), 4.17 (s, 1H), 3.34 (m, 1H), 3.16 (d, J=9 Hz, 1H), 2.92 (m, 1H), 2.80 (d, J=9 Hz, 1H), 2.31 (m, 2H). $^{13}$C NMR (75 MHz, CDCl$_3$) δ (ppm) 208.91, 159.72, 144.01, 143.35, 142.99, 131.63, 128.51, 128.48, 127.30, 127.23, 127.02, 126.96, 74.38, 56.08, 55.46, 50.10, 42.35. MS (ES+) m/z: 366.2 (M+H$^+$).

Example 14

2,5-dibenzyl-(3a,6a-cis)-1,2,3,3a-tetrahydrocyclopenta[c]pyrrol-4(6aH)-one

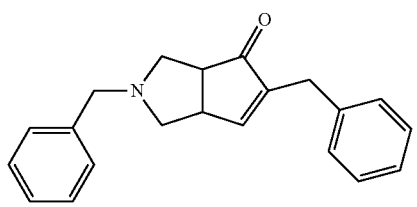 [SMILES: O=C1C(Cc2ccccc2)=CC2CN(Cc3ccccc3)CC12]

From 3-phenyl-1-propyne (37 mg, 0.31 mmol), Co$_2$(CO)$_8$ (107 mg, 0.31 mmol), 1-benzyl-3-pyrroline (50 mg, 0.31 mmol), dimethylsulphoxide (86 mg, 1.1 mmol) and 1,2-dichloroethane (2 ml). Purification: silica gel, hexane:ethyl acetate (10:1), afforded the product (44 mg, 46%) as yellow oil.

$^1$H NMR (400 MHz, CDCl$_3$): δ (ppm) 7.33-7.15 (m, 10H), 7.01 (d, J=3 Hz, 1H), 3.55 (AB system, 2H), 3.49 (AB system, 2H), 3.23 (m, 1H), 3.10 (d, J=9 Hz, 1H), 2.79 (m, 1H), 2.70 (d, J=9 Hz, 1H), 2.36 (t, J=9 Hz, 1H), 2.25 (t, J=9 Hz, 1H). $^{13}$C NMR (75 MHz, CDCl$_3$) δ (ppm) 210.51, 160.12, 146.32, 138.92, 138.59, 128.80, 128.43, 128.36, 128.17, 126.88, 126.18, 58.84, 56.71, 55.77, 49.21, 43.13, 31.13. MS (ES+) m/z: 304.2 (M+H$^+$).

Example 15

2-(4-fluorobenzyl)-5-phenyl-(3a,6a-cis)-1,2,3,3a-tetrahydrocyclopenta[c]pyrrol-4(6aH)-one

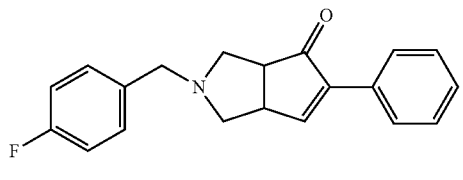 [SMILES: O=C1C(c2ccccc2)=CC2CN(Cc3ccc(F)cc3)CC12]

From phenylacetylene (29 mg, 0.28 mmol), Co$_2$(CO)$_8$ (107 mg, 0.31 mmol), 1-(4-fluoro)benzyl-3-pyrroline (50 mg, 0.28 mmol), dimethylsulphoxide (77 mg, 1.1 mmol) and 1,2-dichloroethane (2 ml). Purification: silica gel, hexane:ethyl acetate (5:1), afforded the product (41 mg, 47%) as yellow oil.

$^1$H NMR (400 MHz, CDCl3): δ (ppm) 7.72 (d, J=7 Hz, 2H), 7.65 (d, J=3 Hz, 1H), 7.41-7.31 (m, 3H), 7.15 (m, 2H), 6.93 (t, J=8.5 Hz, 2H), 3.58-3.45 (AB system, 2H), 3.37 (m, 1H), 3.17 (d, J=9 Hz, 1H), 2.94 (m, 1H), 2.82 (d, J=9 Hz, 1H), 2.40 (t, J=9 Hz, 1H), 2.35 (t, J=9 Hz, 1H). $^{13}$C NMR (75 MHz, CDCl$_3$) δ (ppm) 208.95, 159.58, 143.74, 134.22, 131.50, 129.96, 129.85, 128.50, 128.35, 127.21, 115.14, 114.81, 58.32, 56.87, 56.02, 50.05, 42.48. MS (ES+) m/z: 308.2 (M+H$^+$).

Example 16

2-benzyl-5-(trimethylsilyl)-(3a,6a-cis)-1,2,3,3a-tetrahydrocyclopenta[c]pyrrol-4(6aH)-one

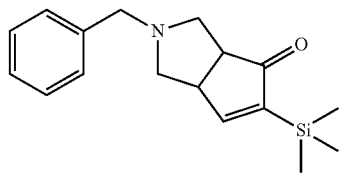 [SMILES: C[Si](C)(C)C1=CC2CN(Cc3ccccc3)CC2C1=O]

From trimethylsilylacetylene (283 mg, 2.82 mmol), Co$_2$(CO)$_8$ (96 mg, 2.82 mmol), 1-benzyl-3-pyrroline (300 mg, 1.88 mmol), dimethylsulphoxide (588 mg, 7.53 mmol) and 1,2-dichloroethane (15 ml). Purification: silica gel, gradient dichloromethane to methanol 8%, afforded the product (150 mg, 28%) as brown oil.

$^1$H NMR (400 MHz, CDCl3): δ (ppm) 7.62 (d, J=2.6 Hz, 1H), 7.26 (m, 5H), 3.57 (AB system, 2H), 3.35 (m, 1H), 3.11 (d, J=9 Hz, 1H), 2.79 (d, J=9 Hz, 1H), 2.74 (m, 1H), 2.37 (m, 2H), 0.24 (s, 9H). $^{13}$C NMR (75 MHz, CDCl$_3$) δ (ppm) 215.10, 172.72, 147.88, 138.99, 128.29, 128.22, 126.86, 58.67, 56.84, 55.90, 49.80, 46.85, −1.76. HRMS calc for M+H$^+$: 286.1627, obs: 286.1619.

Example 17

2-benzyl-(3a,6a-cis)-1,2,3,3a-tetrahydrocyclopenta[c]pyrrol-4(6aH)-one

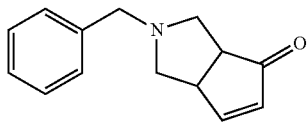 [SMILES: O=C1C=CC2CN(Cc3ccccc3)CC12]

To a solution of 2-benzyl-5-(trimethylsilyl)-1,2,3,3a-tetrahydrocyclopenta[c]pyrrol-4(6-aH)-one (50 mg, 0.17 mmol) in methanol (3 ml), $K_2CO_3$ (25 mg, 0.17 mml) was added and the mixture was stirred at r.t. for 18 h. Water was added and extracted with ethyl acetate, washed with saturated solution of NaCl, dried over $Na_2SO_4$, filtered and concentrated. Purification by flash chromatography: silica gel, gradient dichloromethane to methanol 1%, afforded the product (18 mg, 48%) as yellow oil.

$^1$H NMR (400 MHz, CDCl3): δ (ppm) 7.56 (dd, $J_1$=2.8 Hz, $J_2$=5.6 Hz, 1H), 7.26 (m, 5H), 6.24 (dd, $J_1$=1.7 Hz, $J_2$=5.6 Hz, 1H), 3.55 (AB system, 2H), 3.38 (m, 1H), 3.10 (d, J=9 Hz, 1H), 2.79 (d, J=9 Hz, 1H), 2.73 (m, 1H), 2.35 (m, 2H). $^{13}$C NMR (75 MHz, $CDCl_3$) δ (ppm) 211.93, 165.69, 138.40, 134.92, 128.51, 128.26, 127.02, 58.90, 56.52, 55.49, 48.58, 45.58. HRMS calc for M+H$^+$: 214.1232, obs: 214.1230.

Example 18

2-benzyl-5-tert-butyl-(3a,6a-cis)-1,2,3,3a-tetrahydrocyclopenta[c]pyrrol-4(6aH)-one

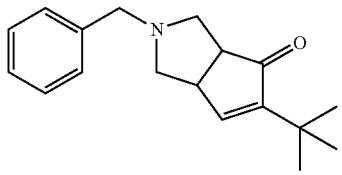 [SMILES: CC(C)(C)C1=CC2CN(Cc3ccccc3)CC2C1=O]

To a solution of 3,3-dimethyl-1-butyne (29 mg, 0.34 mmol) in 1,2-dichloroethane (1 ml) cooled at 0° C. was added $Co_2(CO)_8$ (118 mg, 0.34 mmol) and the mixture was stirred 15 min at 0° C. and 40 minutes at room temperature. A solution of 1-benzyl-3-pyrroline (50 mg, 0.31 mmol) in 1,2-dichloroethane (1 ml) and dimethylsulfoxide (72 μl, 1.01 mmol) were added and the mixture was heated at 83° C. for 20 hours. The reaction mixture was filtered through celite and washed with $CH_2Cl_2$. The filtrate was concentrated and the crude was purified by flash chromatography: silica gel, dichloromethane, to afforded the product (11 mg, 13%) as yellow oil.

$^1$H NMR (400 MHz, CDCl3): δ (ppm) 7.29-7.17 (m, 5H), 7.08 (d, J=3 Hz, 1H), 3.59-3.47 (AB system, 2H), 3.17 (m, 1H), 3.04 (d, J=9 Hz, 1H), 2.72 (m, 1H), 2.68 (d, J=9 Hz, 1H), 2.35 (t, J=9 Hz, 1H), 2.30 (t, J=9 Hz, 1H), 1.20 (s, 9H). $^{13}$C NMR (75 MHz, $CDCl_3$) δ (ppm) 209.28, 156.44, 154.52, 128.27, 128.19, 126.88, 58.69, 58.78, 56.15, 50.23, 42.00, 31.72, 28.33, MS (EI+) m/z: 269.17 (M$^+$).

Example 19

2-benzyl-5-phenyl-(3a,6a-cis)-1,2,3,3a-hexahydrocyclopenta[c]pyrrol-4(5H)-one

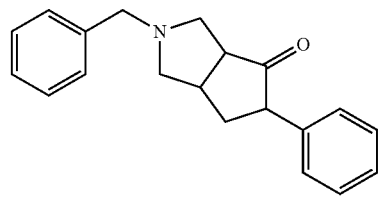 [SMILES: O=C1C(c2ccccc2)CC2CN(Cc3ccccc3)CC12]

A mixture of 2-benzyl-5-phenyl-1,2,3,3a-tetrahydrocyclopenta[c]pyrrol-4(6aH)-one (100 mg, 0.34 mmol), and palladium hydroxide (20 mg, 0.14 mmol) in ethanol (8 ml), was stirred under $H_2$ atmosphere at r.t. for 4 h. Purification by flash chromatography: silica gel, gradient hexane to hexane:ethyl acetate (5:1) afforded the product (47 mg, 47%) as yellow oil. Mixture of diastereomers.

$^1$H NMR (400 MHz, CDCl3): δ (ppm) 7.39-7.15 (m, 20H), 3.77 (d, J=10 Hz, 1H), 3.68 (t, J=14 Hz, 2H), 3.56 (m, 3H), 3.27 (d, J=9 Hz, 1H), 3.08 (d, J=9 Hz, 1H), 2.96 (m, 1H), 2.81 (m, 5H), 2.66 (m, 1H), 2.55 (m, 2H), 2.32 (m, 4H), 1.95 (m, 1H). MS (ES+) 292.2 (M+H$^+$).

General procedure for the 1,4-addition of organolithium and organomagnesium to the enones catalyzed by Cu: To a suspension of CuI (0.2 or 1 eq.) in diethylether, under Ar, cooled at −50° C., the organolithium or organomagnesium reagent was added and the mixture was stirred for 30 min at −50° C. After this time, a solution of the enone (1 eq.) in diethylether was added via cannula to the suspension at −50° C. Stirring was continued for 30 min or until no starting material was observed. The reaction mixture was quenched with a solution of $NH_4Cl/NH_3$ 10% and allowed to reach to r.t. Layers was separated and the aqueous phase was extracted with diethylether. The combined organic phases were washed with $NH_4Cl/NH_3$ 10%, dried over $Mg_2SO_4$, filtered and concentrated to dryness. Purification by flash chromatography.

Example 20

((R,S)-5,6)-2-benzyl-6-methyl-5-phenyl-(3a,6a-cis)-1,2,3,3a-tetrahydrocyclopenta[c]pyrrol-4(1H,2H,5H)-one

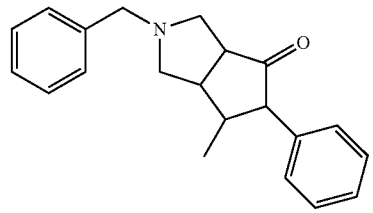 [SMILES: CC1C(c2ccccc2)C(=O)C2CN(Cc3ccccc3)CC21]

From CuI (66 mg, 0.34 mmol), MeLi (0.43 ml, 1.6M solution in hexanes), 2-benzyl-5-phenyl-1,2,3,3a-tetrahydrocyclopenta[c]pyrrol-4(6aH)-one (100 mg, 0.34 mmol) and diethylether (5 ml). The product was obtained as yellow oil (76 mg, 72%). No additional purification was needed.

$^1$H NMR (400 MHz, CDCl3): δ (ppm) 7.38-7.20 (m, 8H), 7.09 (m, 2H), 3.70-3.52 (AB system, 2H), 3.31 (d, J=9 Hz, 1H), 3.13 (d, J=9 Hz, 1H), 2.94 (m, 1H), 2.83 (d, J=9 Hz, 1H), 2.42 (m, 1H), 2.32 (m, 3H), 2.15 (m, 1H), 1.09 (d, J=8.5 Hz, 3H). FIRMS (ES+) m/z: calcd for $C_{21}H_{24}NO$ (M+H$^+$): 306.1858; found: 306.1854.

Example 21

((R,S)-5,6)-2-benzyl-6-butyl-5-phenyl-(3a,6a-cis)-1,2,3,3a-hexahydrocyclopenta[c]pyrrol-4(5H)-one

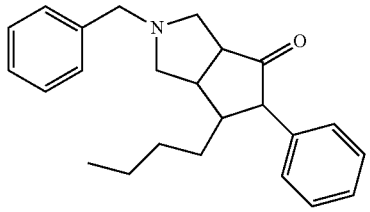 [SMILES: CCCCC1C(c2ccccc2)C(=O)C2CN(Cc3ccccc3)CC21]

From CuI (66 mg, 0.34 mmol), n-BuLi (0.43 ml, 1.6M solution in hexanes), 2-benzyl-5-phenyl-1,2,3,3a-tetrahydrocyclopenta[c]pyrrol-4(6aH)-one (50 mg, 0.17 mmol) and diethylether (5 ml) Purification by flash chromatography: silica gel, gradient hexane to hexane:ethyl acetate (2:1) afforded the product (34 mg, 28%) as yellow oil.

$^1$H NMR (400 MHz, CDCl3): δ (ppm) 7.40-7.20 (m, 8H), 7.11 (m, 2H), 3.60 (AB system, 2H), 3.29 (d, J=9 Hz, 1H), 3.20 (d, J=9 Hz, 1H), 2.94 (t, J=9 Hz, 1H), 2.83 (d, J=9 Hz, 1H), 2.53 (m, 1H), 2.38 (m, 1H), 2.33 (t, J=9 Hz, 1H), 2.14 (m, 1H), 1.58 (m, 1H), 1.40 (m, 1H), 1.20-1.11 (m, 4H), 0.78 (t, J=7 Hz, 3H). MS (ES+) m/z: 348.2 (M+H$^+$).

Example 22

((R,S)-5,6)-2-benzyl-6-ethyl-5-phenyl-(3a,6a-cis)-1,2,3,3a-hexahydracyclopenta[c]pyrrol-4(5H)-one

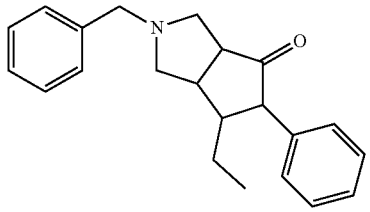 [SMILES: CCC1C(c2ccccc2)C(=O)C2CN(Cc3ccccc3)CC21]

From CuI (13 mg, 0.07 mmol), Ethylmagnesium chloride (0.15 ml, 25% solution in THF), 2-benzyl-5-phenyl-1,2,3,3a-tetrahydrocyclopenta[c]pyrrol-4(6aH)-one (100 mg, 0.34 mmol) and diethylether (5 ml). Purification by flash chromatography: silica gel, gradient hexane to hexane:ethyl acetate (3:1) afforded the product (17 mg, 15%) as yellow oil.

$^1$H NMR (400 MHz, CDCl3): δ (ppm) 7.40-7.20 (m, 8H), 7.12 (m, 2H), 3.62 (AB system, 2H), 3.30 (d, J=9 Hz, 1H), 3.23 (dd, J$_1$=13 Hz, J$_2$=1.5 Hz, 1H), 2.95 (t, J=9 Hz, 1H), 2.85 (d, J=9 Hz, 1H), 2.54 (m, 1H), 2.38 (m, 2H), 2.33 (t, J=9 Hz, 1H), 2.10 (m, 1H), 1.66 (m, 1H), 1.43 (m, 1H), 0.86 (t, J=7 Hz, 3H). HRMS calc for M+H: 320.2014, obs: 320.2019.

Example 23

((R,S)-5,6)-2-benzyl-6-Isopropyl-5-phenyl-(3a,6a-cis)-1,2,3,3a-hexahydrocyclopenta[c]pyrrol-4(5H)-one

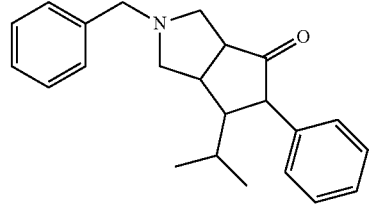 [SMILES: CC(C)C1C(c2ccccc2)C(=O)C2CN(Cc3ccccc3)CC21]

From CuI (329 mg, 1.72 mmol), Isopropylmagnesium chloride (0.95 ml, 2.0M solution in THF), 2-benzyl-5-phenyl-1,2,3,3a-tetrahydrocyclopenta[c]pyrrol-4(6aH)-one (500 mg, 1.72 mmol) and diethylether (11 ml). Purification by flash chromatography: silica gel, gradient hexane to hexane: ethyl acetate (3:1) afforded the product (250 mg, 50%) as yellow oil. Mixture of diastereomers.

5,6-cis diastereomer $^1$H NMR (400 MHz, CDCl3): δ (ppm) 7.40-7.20 (m, 8H), 7.11 (m, 2H), 3.61 (AB system, 2H), 3.39 (d, J=13 Hz, 1H), 3.10 (m, 1H), 2.94 (m, 1H), 2.85 (m, 2H), 2.73 (m, 1H), 2.62 (t, J=10 Hz, 1H), 2.30 (m, 1H), 1.78 (m, 1H), 0.93 (d, J=7 Hz, 3H), 0.59 (d, J=7 Hz, 3H). MS (ES+) m/z: 334.2 (M+H).

Example 24

((R,S)-5,6)-2-benzyl-5-phenyl-6-propyl-(3a,6a-cis)-1,2,3,3a-hexahydrocyclopenta[c]pyrrol-4(5H)-one

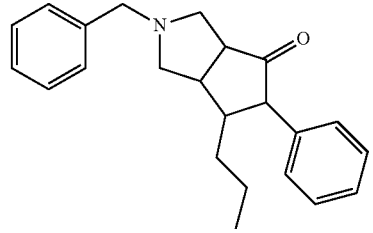 [SMILES: CCCC1C(c2ccccc2)C(=O)C2CN(Cc3ccccc3)CC21]

From CuI (10 mg, 0.052 mmol), propylmagnesium chloride (0.06 ml, 2.0M solution in THF), 2-benzyl-5-phenyl-1,2,3,3a-tetrahydrocyclopenta[c]pyrrol-4(6aH)-one (30 mg, 0.103 mmol) and diethylether (6 ml). The product was obtained as mixture of diastereomers. Purification by HPLC: C18-sunfire, acetonitrile:water (6:4), 25 ml/min.

5,6-cis diastereomer $^1$H NMR (400 MHz, CDCl3): δ (ppm) 7.36-7.22 (m, 8H), 7.08 (m, 2H), 3.60 (AB system, 2H), 3.34 (d, J=13 Hz, 1H), 2.96 (m, 3H), 2.84 (m, 1H), 2.63 (m, 1H), 2.48 (d, J=10 Hz, 1H), 2.39 (m, 1H), 1.36 (m, 3H), 1.15 (m, 1H), 0.80 (t, J=7 Hz, 3H). HRMS calc for M+H: 334.2171, obs: 334.2159.

5,6-trans diastereomer $^1$H NMR (400 MHz, CDCl3): δ (ppm) 7.36-7.22 (m, 8H), 7.11 (m, 2H), 3.61 (AB system, 2H), 3.28 (d, J=10 Hz, 1H), 3.20 (dd, J$_1$=1.7 Hz, J$_2$=12.6 Hz, 1H), 2.94 (m, 1H), 2.82 (d, J=9 Hz, 1H), 2.51 (m, 1H), 2.35 (m, 2H), 2.15 (m, 1H), 1.34 (m, 3H), 1.16 (m, 1H), 0.80 (t, J=7 Hz, 3H). HRMS calc for M+H: 334.2171, obs: 334.2159.

Example 25

((R,S)-5,6)-2-benzyl-6-ethyl-5-(4-fluorophenyl)-(3a,6a-cis)-1,2,3,3a-hexahydrocyclopenta[c]pyrrol-4(5H)-one

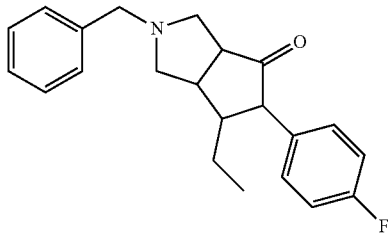 [SMILES: CCC1C(c2ccc(F)cc2)C(=O)C2CN(Cc3ccccc3)CC21]

From CuI (31 mg, 0.16 mmol), ethylmagnesium chloride (0.2 ml, 25% solution in THF), 2-benzyl-5-(4-fluorophenyl)-1,2,3,3a-tetrahydrocyclopenta[c]pyrrol-4(6aH)-one (100 mg, 0.32 mmol) and diethylether (6 ml). Purification by HPLC: C18-sunfire, acetonitrile:water (6:4), 18 mL/min.

$^1$H NMR (400 MHz, CDCl3): δ (ppm) 7.30-7.14 (m, 5H), 6.97 (m, 4H), 3.54 (AB system, 2H), 3.21 (d, J=9 Hz, 1H), 3.14 (dd, J$_1$=1.5 Hz, J$_2$=12.5 Hz, 1H), 2.86 (t, J=9 Hz, 1H), 2.76 (d, J=9 Hz, 2H), 2.45 (m, 1H), 2.27 (m, 1H), 1.95 (m, 1H), 1.56 (m, 1H), 1.35 (m, 1H), 0.78 (t, J=7 Hz, 3H). HRMS calc for M+H: 338.1920, obs: 338.1928.

Example 26

((R,S)-5,6)-2-benzyl-5-(4-fluorophenyl)-6-propyl-(3a,6a-cis)-1,2,3,3a-hexahydrocyclopenta[c]pyrrol-4(5H)-one

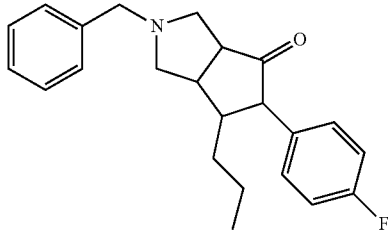 [SMILES: CCCC1C(c2ccc(F)cc2)C(=O)C2CN(Cc3ccccc3)CC21]

From CuI (31 mg, 0.16 mmol), propylmagnesium chloride (0.19 ml, 2.0M solution in THF), 2-benzyl-5-(4-fluorophenyl)-1,2,3,3a-tetrahydrocyclopenta[c]pyrrol-4(6aH)-one (100 mg, 0.32 mmol) and diethylether (6 ml). The product was obtained as mixture of diastereomers. Purification by HPLC: C18-sunfire, acetonitrile:water (6:4), 25 ml/min.

5,6-cis diastereomer $^1$H NMR (400 MHz, CDCl3): δ (ppm) 7.28 (m, 5H), 7.03 (m, 4H), 3.60 (AB system, 2H), 3.34 (d, J=13.6 Hz, 1H), 2.95 (m, 3H), 2.83 (m, 1H), 2.61 (m, 1H), 2.46 (t, J=9 Hz, 1H), 2.33 (m, 1H), 1.36 (m, 3H), 1.15 (m, 1H), 0.81 (t, J=7 Hz, 3H). HRMS calc for M+H: 352.2077, obs: 352.2061.

5,6-trans diastereomer $^1$H NMR (400 MHz, CDCl3): δ (ppm) 7.28 (m, 5H), 7.03 (m, 4H), 3.60 (AB system, 2H), 3.28 (d, J=13.6 Hz, 1H), 3.19 (m, 1H), 2.94 (t, J=9 Hz, 1H), 2.82 (d, J=9 Hz, 1H), 2.51 (m, 1H), 2.34 (m, 2H), 2.08 (m, 1H), 1.54 (m, 1H), 1.36 (m, 2H), 1.16 (m, 1H), 0.80 (t, J=7 Hz, 3H). HRMS calc for M+H: 352.2077, obs: 352.2066.

Example 27

((R,S)-5,6)-2-benzyl-6-butyl-5-(4-fluorophenyl)-(3a,6a-cis)-1,2,3,3a-hexahydrocyclopenta[c]pyrrol-4(5H)-one

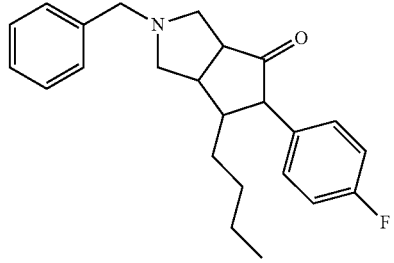 [SMILES: CCCCC1C(c2ccc(F)cc2)C(=O)C2CN(Cc3ccccc3)CC21]

From CuI (31 mg, 0.16 mmol), n-BuLi (0.13 ml, 2.5M solution in hexanes), 2-benzyl-5-(4-fluorophenyl)-1,2,3,3a-tetrahydrocyclopenta[c]pyrrol-4(6aH)-one (100 mg, 0.32 mmol) and diethylether (3 ml). The product was obtained as mixture or diastereomers. Purification by HPLC: C18-sunfire, acetonitrile:water (6:4), 25 ml/min.

5,6-cis diastereomer $^1$H NMR (400 MHz, CDCl3): δ (ppm) 7.28 (m, 5H), 7.03 (m, 4H), 3.59 (AB system, 2H), 3.34 (d, J=13.6 Hz, 1H), 2.96 (m, 3H), 2.83 (m, 1H), 2.60 (m, 1H), 2.48 (t, J=9 Hz, 1H), 2.31 (m, 1H), 1.40 (m, 1H), 1.20 (m, 5H), 0.80 (t, J=7 Hz, 3H). HRMS calc for M+H: 366.2233, obs: 366.2220.

5,6-trans diastereomer $^1$H NMR (400 MHz, CDCl3): δ (ppm) 7.28 (m, 5H), 7.05 (m, 4H), 3.61 (AB system, 2H), 3.28 (d, J=9 Hz, 1H), 3.19 (dd, J$_1$=1.5 Hz, J$_2$=13 Hz, 1H), 2.93 (t, J=9 Hz, 1H), 2.82 (d, J=9 Hz, 1H), 2.51 (m, 1H), 2.33 (m, 2H), 2.07 (m, 1H), 1.56 (m, 1H), 1.39 (m, 1H), 1.19 (m, 4H), 0.79 (t, J=7 Hz, 3H). HRMS calc for M+H: 366.2233, obs: 366.2221.

Example 28

((R,S)-5,6)-2-benzyl-5-(4-fluorophenyl)-6-methyl-(3a,6a-cis)-1,2,3,3a-hexahydrocyclopenta[c]pyrrol-4(5H)-one

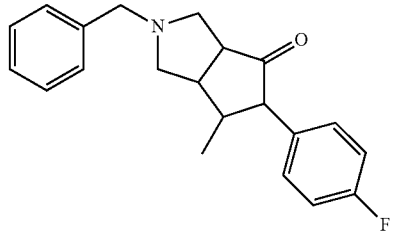 [SMILES: CC1C(c2ccc(F)cc2)C(=O)C2CN(Cc3ccccc3)CC21]

From CuI (330 mg, 0.16 mmol), Methyl lithium (0.11 ml, 1.6M solution in hexanes), 2-benzyl-5-(4-fluorophenyl)-1,2,3,3a-tetrahydrocyclopenta[c]pyrrol-4(6aH)-one (500 mg, 1.72 mmol) and diethylether (11 ml). The product was obtained as mixture of diastereomers. Purification by flash chromatography: silica gel, gradient hexane to hexane:ethyl acetate 1:1.

5,6-cis diastereomer $^1$H NMR (400 MHz, CDCl3): δ (ppm) 7.28 (m, 5H), 7.04 (m, 4H), 3.59 (AB system, 2H), 3.31 (d, J=13.6 Hz, 1H), 2.97 (m, 2H), 2.88 (m, 2H), 2.61 (t, J=9 Hz, 1H), 2.41 (m, 2H), 1.03 (d, J=7 Hz, 3H). MS (ES+) m/z: 324.2 (M+H).

5,6-trans diastereomer $^1$H NMR (400 MHz, CDCl3): δ (ppm) 7.32 (m, 5H), 7.08 (m, 4H), 3.64 (AB system, 2H), 3.33 (d, J=9 Hz, 1H), 3.15 (dd, $J_1$=1.5 Hz, $J_2$=13 Hz, 1H), 2.97 (t, J=9 Hz, 1H), 2.87 (d, J=9 Hz, 1H), 2.45 (m, 1H), 2.35 (m, 2H), 2.12 (m, 1H), 1.12 (d, J=7 Hz, 3H). MS (ES+) m/z: 324.2 (M+H).

Example 29

((R,S)-5,6)-2-benzyl-5,6-dibutyl-(3a,6a-cis)-1,2,3, 3a-hexahydrocyclopenta[c]pyrrol-4(5H)-one

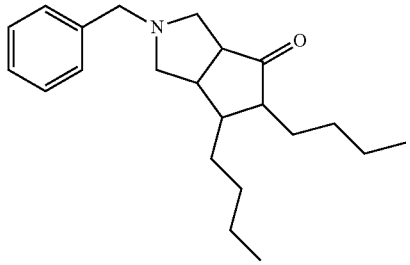 [SMILES: CCCCC1C(=O)C2CN(Cc3ccccc3)CC2C1CCCC]

From CuI (141 mg, 0.74 mmol), n-buthyl lithium (0.3 ml, 2.5M solution in hexanes), 2-benzyl-5-butyl-1,2,3,3a-tetrahydrocyclopenta[c]pyrrol-4(6aH)-one (200 mg, 0.74 mmol) and diethylether (12 ml). Purification by flash chromatography: silica gel, gradient hexane to hexane:ethyl acetate 1:1.

$^1$H NMR (400 MHz, CDCl3): δ (ppm) 7.25 (m, 5H), 3.55 (AB system, 2H), 3.10 (d, J=9 Hz, 1H), 2.75 (t, J=9 Hz, 1H), 2.69 (d, J=8 Hz, 1H), 2.36 (m, 2H), 2.25 (t, J=9 Hz, 1H), 1.96 (m, 1H), 1.73-1.19 (m, 13H), 0.90 (m, 6H). MS (ES+) m/z: 328.2 (M+H).

Example 30

((R,S)-5,6)-2-benzyl-5,6-dibutyl-(3a,6a-cis)-1,2,3, 3a-hexahydrocyclopenta[c]pyrrol-4(5H)-one

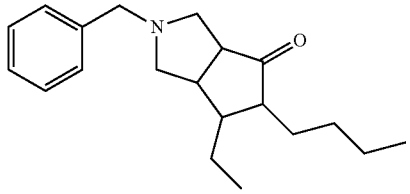 [SMILES: CCCCC1C(=O)C2CN(Cc3ccccc3)CC2C1CC]

From CuI (33 mg, 0.17 mmol), ethylmagnesium chloride (0.13 ml, 25% solution in THF), 2-benzyl-5-butyl-1,2,3,3a-tetrahydrocyclopenta[c]pyrrol-4(6aH)-one (100 mg, 0.34 mmol) and diethylether (6 ml). The product was obtained as mixture of diastereomers. Purification by HPLC: C18-sunfire, acetonitrile:water (6:4), 25 ml/min.

5,6-cis diastereomer $^1$H NMR (400 MHz, CDCl3): δ (ppm) 7.25 (m, 5H), 3.54 (AB system, 2H), 3.10 (dd, $J_1$=1.8 Hz, $J_2$=9 Hz, 1H), 2.73 (m, 2H), 2.37 (m, 2H), 2.26 (t, J=9 Hz, 1H), 1.98 (m, 1H), 1.75-1.20 (m, 9H), 0.93 (m, 6H). HRMS calc for M+H: 300.2327, obs: 300.2330.

5,6-trans diastereomer $^1$H NMR (400 MHz, CDCl3): δ (ppm) 7.25 (m, 5H), 3.54 (AB system, 2H), 2.88 (m, 1H), 2.81 (m, 1H), 2.71 (m, 1H), 2.63 (m, 2H), 2.44 (t, J=9 Hz, 1H), 2.07 (m, 1H), 1.86 (m, 1H), 1.71 (m, 1H), 1.52 (m, 2H), 1.30 (m, 5H), 0.91 (m, 6H). HRMS calc for M+H: 300.2327, obs: 300.2325.

Example 31

((R,S)-5,6)-2-benzyl-5-butyl-6-methyl-(3a,6a-cis)-1, 2,3,3a-hexahydrocyclopenta[c]pyrrol-4(5H)-one

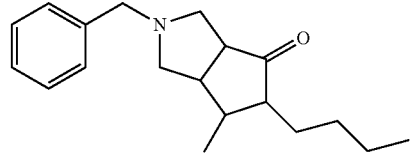 [SMILES: CCCCC1C(=O)C2CN(Cc3ccccc3)CC2C1C]

From CuI (141 mg, 0.74 mmol), methylmagnesium bromide (0.24 ml, 3.0M solution in diethylether), 2-benzyl-5-butyl-1,2,3,3a-tetrahydrocyclopenta[c]pyrrol-4(6aH)-one (200 mg, 0.74 mmol) and diethylether (10 ml). Purification by flash chromatography: silica gel, gradient hexane to hexane:ethyl acetate 1:3.

$^1$H NMR (400 MHz, CDCl3): δ (ppm) 7.25 (m, 5H), 3.53 (AB system, 2H), 2.27 (m, 3H), 2.63 (m, 2H), 2.38 (t, J=9 Hz, 1H), 2.04 (m, 2H), 1.61-1.18 (m, 6H), 1.08 (d, J=6 Hz, 3H), 0.90 (m, 3H). MS (ES+) m/z: 286.2 (M+H).

Example 32

((R,S)-5,6)-2-benzyl-5-butyl-6-phenyl-(3a,6a-cis)-1, 2,3,3a-hexahydrocyclopenta[c]pyrrol-4(5H)-one

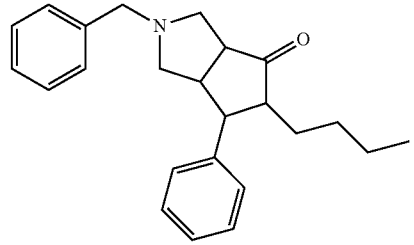 [SMILES: CCCCC1C(=O)C2CN(Cc3ccccc3)CC2C1c1ccccc1]

From CuI (70 mg, 0.37 mmol), phenyl lithium (0.39 ml, 1.9M solution in dibuthylether), 2-benzyl-5-butyl-1,2,3,3a-tetrahydrocyclopenta[c]pyrrol-4(6aH)-one (100 mg, 0.37 mmol) and diethylether (4 ml). The product was obtained as mixture of diastereomers. Purification by HPLC: C18-sunfire, acetonitrile:water (6:4), 25 ml/min.

5,6-cis diastereomer $^1$H NMR (400 MHz, CDCl3): δ (ppm) 7.30-7.10 (m, 10H), 3.53 (AB system, 2H), 3.24 (m, 1H), 3.07 (d, J=9 Hz, 1H), 2.76 (m, 1H), 2.71 (d, J=9 Hz, 1H), 2.35 (t, J=9 Hz, 1H), 2.28 (t, J=9 Hz, 1H), 2.19 (m, 2H), 1.60 (m, 2H), 1.48 (m, 2H), 1.35 (m, 2H), 0.92 (t, J=7 Hz, 3H). HRMS calc for M+H: 348.2327, obs: 348.2321.

5,6-trans diastereomer NMR (400 MHz, CDCl3): δ (ppm) 7.32 (m, 4H), 7.25 (m, 3H), 7.17 (m, 3H), 6.96 (m, 4H), 3.78 (dd, J₁=1.5 Hz, J₂=13 Hz, 1H), 3.65 (AB system, 2H), 3.39 (d, J=9 Hz, 1H), 3.26 (m, 1H), 3.12 (t, J=9 Hz, 1H), 2.93 (m, 2H), 2.38 (t, J=9 Hz, 1H), 2.25 (m, 1H). HRMS calc for M+H: 386.1920, obs: 386.1910.

Example 33

((R,S)-5,6)-2-benzyl-5-(4-chlorophenyl)-6-methyl-(3a,6a-cis)-1,2,3,3a-hexahydrocyclopenta[c]pyrrol-4(5H)-one

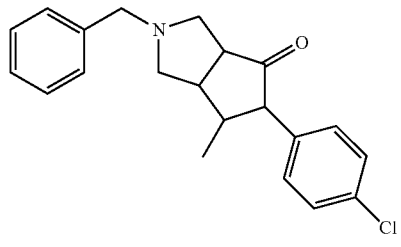 [SMILES: CC1C(c2ccc(Cl)cc2)C(=O)C2CN(Cc3ccccc3)CC21]

From CuI (18 mg, 0.09 mmol), methyl lithium (0.07 ml, 1.6M solution in hexanes), 2-benzyl-5-(4-chlorophenyl)-1,2,3,3a-tetrahydrocyclopenta[c]pyrrol-4(6aH)-one (50 mg, 0.74 mmol) and diethylether (4 ml). Purification by flash chromatography: silica gel, gradient hexane to hexane:ethyl acetate 1:3.

¹H NMR (400 MHz, CDCl3): δ (ppm) 7.30 (m, 7H), 7.02 (m, 2H), 3.59 (AB system, 2H), 3.31 (d, J=13 Hz, 1H), 2.98 (m, 2H), 2.88 (m, 2H), 2.61 (m, 1H), 2.42 (m, 2H), 1.02 (d, J=7 Hz, 3H). HRMS calc for M+H: 340.1468, obs: 340.1454.

Example 34

((R,S)-5,6)-2-benzyl-5-(4-fluorophenyl)-6-phenyl-(3a,6a-cis)-1,2,3,3a-hexahydrocyclopenta[c]pyrrol-4(5H)-one

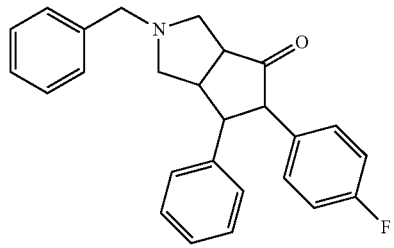 [SMILES: O=C1C2CN(Cc3ccccc3)CC2C(c2ccccc2)C1c1ccc(F)cc1]

From CuI (62 mg, 0.32 mmol), phenyl lithium (0.30 ml, 1.9M solution in dibuthylether), 2-benzyl-5-(4-fluorophenyl)-1,2,3,3a-tetrahydrocyclopenta[c]pyrrol-4(6aH)-one (100 mg, 0.32 mmol) and diethylether (4 ml). Purification by flash chromatography: silica gel, gradient hexane to hexane:ethyl acetate 1:1.

¹H NMR (400 MHz, CDCl3): δ (ppm) 7.36-7.00 (m, 15H), 3.80 (d, J=13 Hz, 1H), 3.65 (AB system, 2H), 3.39 (d, J=10 Hz, 1H), 3.35 (m, 1H), 3.11 (t, J=9 Hz, 1H), 2.92 (m, 1H), 2.39 (t, J=9 Hz, 1H), 2.25 (m, 1H). HRMS calc for M+H: 368.2014, obs: 368.2025.

General procedure for the 1,4-addition of arylboronic acids catalyzed by Rh: A mixture of enone (1 eq), arylboronic acid (2.5 eq), [RhCl(COD)]₂ complex (0.03 eq) and LiOH (5 eq) in dioxane:water (4:1), under Ar atmosphere in a sealed tube, was irradiated with microwaves (max power 150 wets) at 150° C. for 30 min or until starting enone is consumed. Saturated solution of NH₄Cl was added and extracted with ethyl acetate, the organic phase was washed with water and sat solution of NaCl, dried over Na₂SO₄, filtered and concentrated. The product was purified by flash chromatography: silica gel, gradient hexane to hexane:ethyl acetate 1:4.

Example 35

((R,S)-5,6)-2-benzyl-5,6-diphenyl-(3a,6a-cis)-1,2,3,3a-hexahydrocyclopenta[c]pyrrol-4(5H)-one

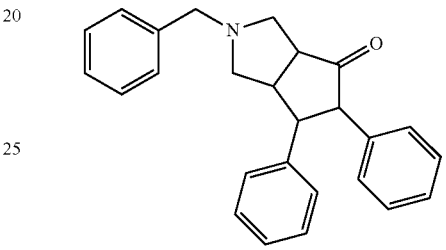

From phenyl boronic acid (63 mg, 0.51 mmol), [RhCl(COD)]₂ (3 mg, 0.006 mmol), 2-benzyl-5-phenyl-1,2,3,3a-tetrahydrocyclopenta[c]pyrrol-4(6aH)-one (60 mg, 0.20 mmol), LiOH (25 mg, 1.03 mmol) and dioxane:water (4:1, 1.2 ml). The product was obtained (30 mg, 15%) as colourless oil.

¹H NMR (400 MHz, CDCl3): δ (ppm) 7.36-7.00 (m, 15H), 3.80 (d, J=13 Hz, 1H), 3.65 (AB system, 2H), 3.39 (d, J=10 Hz, 1H), 3.35 (m, 1H), 3.11 (t, J=9 Hz, 1H), 2.92 (m, 1H), 2.39 (t, J=9 Hz, 1H), 2.25 (m, 1H). HRMS calc for M+H: 368.2014, obs: 368.2025.

Example 36

((R,S)-5,6)-2-benzyl-6-(3,5-dimethylphenyl)-5-phenyl-(3a,6a-cis)-1,2,3,3a-hexahydro cyclopenta[c]pyrrol-4(5H)-one

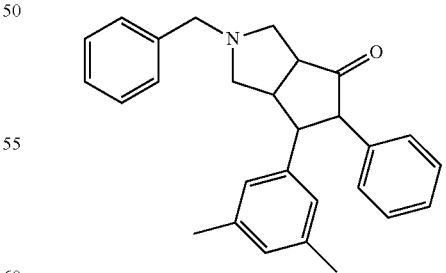

From 3,5-dimethylphenyl boronic acid (78 mg, 0.51 mmol), [RhCl(COD)]₂ (3 mg, 0.006 mmol), 2-benzyl-5-phenyl-1,2,3,3a-tetrahydrocyclopenta[c]pyrrol-4(6aH)-one (60 mg, 0.20 mmol), LiOH (25 mg, 1.03 mmol) and dioxane:water (4:1, 1.2 ml). The product was obtained (22 mg, 26%) as colourless oil.

¹H NMR (400 MHz, CDCl3): δ (ppm) 7.33 (m, 3H), 7.25 (m, 5H), 7.04 (m, 2H), 6.79 (m, 3H), 3.80 (d, J=13 Hz, 1H), 3.64 (AB system, 2H), 3.36 (d, J=9 Hz, 1H), 3.29 (m, 1H), 3.09 (t, J=9 Hz, 1H), 2.93 (d, J=9 Hz, 1H), 2.88 (m, 1H), 2.23 (s, 6H). HRMS calc for M+H: 396.2327, obs: 396.2335.

Example 37

((R,S)-5,6)-2-benzyl-6-(4-methoxyphenyl)-5-phenyl-(3a,6a-cis)-1,2,3,3a-hexahydro cyclopenta[c]pyrrol-4(5H)-one

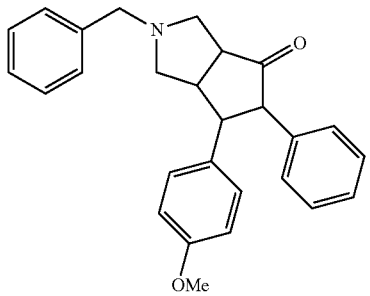 [SMILES: COc1ccc(C2C(c3ccccc3)C(=O)C3CN(Cc4ccccc4)CC32)cc1]

From 4-methoxyphenyl boronic acid (157 mg, 1.03 mmol), [RhCl(COD)]₂ (6 mg, 0.012 mmol), 2-benzyl-5-phenyl-1,2,3,3a-tetrahydrocyclopenta[c]pyrrol-4(6aH)-one (120 mg, 0.41 mmol), LiOH (50 mg, 2.07 mmol) and dioxane:water (4:1, 2 ml). The product was obtained (85 mg, 51%) as colourless oil.

¹H NMR (400 MHz, CDCl3): δ (ppm) 7.41-7.21 (m, 8H), 7.11 (m, 4H), 6.83 (m, 2H), 3.80 (d, J=13 Hz, 1H), 3.77 (s, 3H), 3.71 (AB system, 2H), 3.44 (d, J=10 Hz, 1H), 3.35 (m, 1H), 3.15 (t, J=9 Hz, 1H), 2.95 (m, 2H), 2.44 (d, J=9 Hz, 1H), 2.31 (m, 1H). HRMS calc for M+H: 398.2120, obs: 398.2137.

Example 38

((R,S)-5,6)-2-benzyl-5-(4-chlorophenyl)-6-phenyl-(3a,6a-cis)-1,2,3,3a-hexahydrocyclopenta[c]pyrrol-4(5H)-one

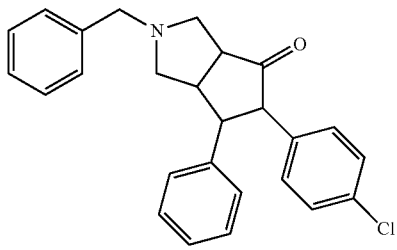 [SMILES: O=C1C2CN(Cc3ccccc3)CC2C(c2ccccc2)C1c1ccc(Cl)cc1]

From phenyl boronic acid (385 mg, 3.0 mmol), [RhCl (COD)]₂ (18 mg, 0.036 mmol), 2-benzyl-5-(4-chlorophenyl)-1,2,3,3a-tetrahydrocyclopenta[c]pyrrol-4(6aH)-one (400 mg, 1.23 mmol), LiOH (151 mg, 6.1 mmol) and dioxane:water (4:1, 9 ml). The product was obtained (160 mg, 32%) as yellow oil.

¹H NMR (400 MHz, CDCl3): δ (ppm) 7.37-7.13 (m, 12H), 6.94 (m, 2H), 3.77 (d, J=13 Hz, 1H), 3.65 (AB system, 2H), 3.39 (d, J=10 Hz, 1H), 3.27 (m, 1H), 3.12 (t, J=9 Hz, 1H), 2.92 (m, 2H), 2.38 (t, J=9 Hz, 1H), 2.25 (m, 1H). HRMS calc for M+H: 402.1625, obs: 402.1606.

Biological Activity

Some representative compounds of the Invention were tested for their activity as sigma (sigma-1 and sigma-2) inhibitors. The following protocols were followed:

Sigma-1

Brain membrane preparation and binding assays for the σ1-receptor were performed as described (DeHaven-Hudkins et al., 1992) with some modifications. In brief, guinea pig brains were homogenized in 10 vols. (w/v) of Tris-HCl 50 mM 0.32 M sucrose, pH 7.4, with a Kinematics Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

Each assay tube contained 10 μL of [³H](+)-pentazocine (final concentration of 0.5 nM), 900 μL of the tissue suspension to a final assay volume of 1 mL and a final tissue concentration of approximately 30 mg tissue net weight/mL. Non-specific binding was defined by addition of a final concentration of 1 μM haloperidol. All tubes were incubated at 37° C. for 150 min before termination of the reaction by rapid filtration over Schleicher & Schuell GF 3362 glass fibre filters [previously soaked in a solution of 0.5% polyethylenimine for at least 1 h]. Filters were then washed with four times with 4 mL of cold Tris-HCl buffer (50 mM, pH 7.4). Following addition of scintillation cocktail, the samples were allowed to equilibrate overnight. The amount of bound radioactivity was determined by liquid scintillation spectrometry using a Wallac Winspectral 1414 liquid scintillation counter. Protein concentrations were determined by the method of Lowry et al. (1951).

Sigma-2

Binding studies for σ2-receptor were performed as described (Radesca et al., 1991) with some modifications. In brief, brains from sigma receptor type I (σ1) knockout mice were homogenized in a volume of 10 mL/g tissue net weight of ice-cold 10 mM Tris-HCl, pH 7.4, containing 320 mM sucrose (Tris-sucrose buffer) with a Potter-Elvehjem homogenizer (10 strokes at 500 r.p.m.) The homogenates were then centrifuged at 1000 g for 10 min at 4° C., and the supernatants were saved. The pellets were resuspended by vortexing in 2 mL/g ice-cold Tris-sucrose buffer and centrifuged again at 1000 g for 10 min. The combined 1000 g supernatants were centrifuged at 31000 g for 15 min at 4° C. The pellets were resuspended by vortexing in 3 mL/g 10 mM Tris-HCl, pH 7.4, and the suspension was kept at 25° C. for 15 min. Following centrifugation at 31000 g for 15 min, the pellets were resuspended by gentle Potter Elvehjem homogenization to a volume of 1.53 mL/g in 10 mM Tris-HCl pH 7.4.

The assay tubes contained 10 μL of [³H]-DTG (final concentration of 3 nM), 400 μL of the tissue suspension (5.3 mL/g in 50 mM Tris-HCl, pH 8.0) to a final assay volume of 0.5 mL. Non-specific binding was defined by addition of a final concentration of 1 μM haloperidol. All tubes were incubated at 25° C. for 120 min before termination of the reaction by rapid filtration over Schleicher & Schuell GF 3362 glass fibre filters [previously soaked in a solution of 0.5% polyethylenimine for at least 1 h]. Filters were washed with three times with 5 mL volumes of cold Tris-HCl buffer (10 mM, pH 8.0). Following addition of scintillation cocktail samples were allowed to equilibrate overnight. The amount of bound radioactivity was determined by liquid scintillation spectrometry using a Wallac Winspectral 1414 liquid scintillation counter. Protein concentrations were determined by the method of Lowry et al. (1951).

REFERENCES

DeHaven-Hudkins, D. L., L. C. Fleissner, and F.Y. Ford-Rice, 1992, "Characterization of the binding of [$^3$H](+)pentazocine to a recognition sites in guinea pig brain", Eur. J. Pharmacol. 227, 371-378.

Radesca, L., W. D. Bowen, and L. Di Paolo, B. R. de Costa, 1991, Synthesis and Receptor Binding of Enantiomeric N-Substituted cis-N-[2-(3,4-Dichlorophenyl)ethyl]-2-(1-pyrrolidinyl)cyclohexylamines as High-Affinity σ Receptor Ligands, J. Med. Chem. 34, 3065-3074.

Lange, F., Codony X., Tover V., Lavado A., Giménez E., Cozar P., Cantero M., Dordal A., Hernández E., Pérez R., Monroy X., Zamanillo D., Guitart X., Montoliu L I., 2003, Generation and phenotypic analysis of sigma receptor type I (Sigma1) knockout mice, European Journal of Neuroscience, Vol. 18, 2188-2196.

Lowry, O. H., N. J. Rosebrough, A. L. Farr, and R. J. Randall, 1951, Protein measurement with the Folin phenol reagent, J. Biol. Chem, 193, 265.

Some of the results obtained are shown in table (I).

TABLE (I)

| Example | % Binding σ1 $10^{-7}$M | % Binding σ1 $10^{-8}$M |
|---|---|---|
| 1 | 79.4 | 46.8 |
| 2 | 40.1 | 38 |
| 3 | 47.3 | 11.3 |
| 4 | 88.9 | 57.4 |
| 5 | 102.3 | 54 |
| 6 | 92.7 | 45.5 |
| 7 | 67.5 | 46.9 |
| 8 | 104.1 | 68.3 |
| 9 | 97.5 | 73.4 |
| 10 | 57.0 | 34.2 |
| 11 | 23.3 | 17.7 |
| 12 | 101.7 | 53.2 |
| 13 | 27.6 | 4.8 |
| 14 | 85.7 | 31.0 |
| 15 | 71.7 | 29.8 |
| 18 | 54.1 | 33.3 |
| 19 | 43.9 | 2.3 |
| 20 | 103.3 | 82.0 |
| 21 | 72.3 | 28.2 |
| 22 | 98.3 | 80.3 |
| 23 | 103.2 | 94.8 |
| 24 cis | 47.4 | 16.7 |
| 24 trans | 76.1 | 25.2 |
| 25 | 83.2 | 37.2 |
| 26 trans | 70.5 | 16.7 |
| 28 cis | 89.6 | 100.5 |
| 29 | 32.5 | −44.3 |
| 30 cis | 91.9 | 65.2 |
| 30 trans | 96.3 | 84.2 |
| 31 | 93.9 | 81.7 |
| 32 cis | 70.3 | 39.8 |
| 32 trans | 99.6 | 78.2 |
| 33 | 95.1 | 69.9 |
| 37 | 56.7 | 39 |
| 38 | 84 | 28 |

The invention claimed is:
1. A method for the treatment of a sigma receptor-mediated disease or condition, said method comprising administering to a subject in need thereof a therapeutically effective amount of substituted bicyclic tetrahydropyrrole compounds of general formula (I)

wherein $R^1$ represents
  a benzyl group in which the methylene moiety of the benzyl group and the aromatic moiety of the benzyl group are independently unsubstituted or substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, NHR', and NR'R", wherein R' and R" for each substituent independently represents a linear or branched $C_{1-6}$-alkyl group, and wherein the aromatic moiety is condensed with or is not condensed with a substituted or unsubstituted mono- or polycyclic ring system; or
  a benzhydryl group which is unsubstituted or substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH and SA;
wherein the bond between Y and Z is saturated (Y—Z), with Y representing C—$RR^{11}R^{12}$; and Z representing CH—$R^6$; or wherein the bond between Y and Z is unsaturated (Y=Z), with Y representing CH and Z representing a C—$R^6$ group;
$R^6$ represents
  an unbranched or branched $C_{1-6}$ alkyl group which is unsubstituted or substituted by one or more substituents independently selected from the group consisting of a F, Cl, I, Br, $CF_3$, $CH_2F$, $CHF_2$, CN, OH, SH, and $NH_2$;
  a phenyl group which is unsubstituted or substituted by one or more substituents independently selected from the group consisting of a $C_{1-4}$ alkyl group, an unsubstituted or substituted phenyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, N(C=O)—OR', NHR', and NR'R", wherein R' and R" for each substituent independently represents a linear or branched $C_{1-6}$— alkyl group; or
  timethylellyl group;
$R^{11}$ represents a hydrogen; and
$R^{12}$ represents
  a linear or branched, saturated or unsaturated, substituted or unsubstituted $C_{1-6}$ aliphatic group; or
  a substituted or unsubstituted phenyl group;
or
  wherein the bond between Y and Z is saturated (Y—Z), with Y representing $CH_2$;
and Z representing CH—$R^6$;
R6 represents
  a phenyl group which is unsubstituted or substituted by one or more substituents independently selected from the group consisting of a $C_{1-4}$ alkyl group, an unsubstituted or substituted phenyl group, a linear or branched $C_{1-6}$; alkoxy group, F, Cl, I, Br, $CF_3$, $CH_2F$, $CHF_2$, CN, OH, SH, $NH_2$, (C=O)R', SR', SOR', $SO_2R'$, N(C=O)—OR', NHR', and NR'R", wherein R' and R" for each substituent independently represents a linear or branched $C_{1-6}$—alkyl group; or a trimethylsilyl group;

optionally in a form of one of the stereoisomers, enantiomers, or diastereomers, a racemate, or a mixture of at least two of the stereoisomers, or a corresponding salt thereof, wherein said disease or condition is a pain disorder.

2. The method according to claim 1, characterized in that $R^1$ represents a benzyl group in which the methylene moiety of the benzyl group and the aromatic moiety of the benzyl group are independently unsubstituted or substituted by one or more substituents independently selected from the group consisting of a $C_{1-4}$ alkyl group, a linear or branched $C_{1-6}$ alkoxy group, F, Cl, I, Br, $CF_3$, $CH_2CN$, OH, SH, $NH_2$, (C=O)R', SR', SOR', $SO_2R'$, NHR', and NR'R", wherein R' and R" for each substituent independently represents a linear or branched $C_{1-6}$—alkyl group, and wherein the aromatic moiety is condensed with or is not condensed with a substituted or unsubstituted mono- or polycyclic ring system; or a benzhydryl group which is unsubstituted or substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH and SH;

wherein the bond between Y and Z is saturated (Y—Z), with Y representing C—$R^{11}R^{12}$; and Z representing CH—$R^6$;

$R^6$ represents an unbranched or branched $C_{1-6}$ alkyl group which is unsubstituted or substituted by one or more substituents independently selected from the group consisting of a F, Cl, I, Br, $CF_3$, $CH_2F$, $CHF_2$, CN, OH, SH, and $NH_2$;

a phenyl group which is unsubstituted or substituted by one or more substituents independently selected from the group consisting of a $C_{1-4}$ alkyl group, an unsubstituted or substituted phenyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, N(C'0)—OR', NHR', and NR'R", wherein R' and R" for each substituent independently represents a linear or branched $C_{1-6}$—alkyl group; or a trimethylsilyl group;

$R^{11}$ represents a hydrogen; and $R^{12}$ represents a linear or branched, saturated or unsaturated, substituted or unsubstituted $C^{1-6}$ aliphatic group; or a substituted or unsubstituted phenyl group;

optionally in a form of one of the stereoisomers, enantiomers, or diastereomers, a racemate, or a mixture of at least two of the stereoisomers, or a corresponding salt thereof.

3. The method according to claim 1, characterized in that $R^1$ represents a benzyl group in which the methylene moiety of the benzyl group and the aromatic moiety of the benzyl group are independently unsubstituted or substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, NHR', and NR'R", wherein R' and R" for each substituent independently represents a linear or branched $C_{1-6}$—alkyl group, and wherein the aromatic moiety is condensed with or is not condensed with a substituted or unsubstituted mono- or polycyclic ring system; or a benzhydryl group which is unsubstituted or substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH and SR;

wherein the bond between Y and Z is unsaturated (Y=Z), with Y representing CH and Z representing a C—$R_6$ group;

$R^6$ represents an unbranched or branched $C_{1-6}$ alkyl group which is unsubstituted or substituted by one or more substituents independently selected from the group consisting of a F, Cl, I, Br, $CF_3$, $CH_2F$, $CHF_2$, CN, OH, SH, and $NH_2$;

a phenyl group which is unsubstituted or substituted by one or more substituents independently selected from the group consisting of a $C_{1-4}$ alkyl group, an unsubstituted or substituted phenyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, N(C=O)—OR', NHR', and NR'R", wherein R' and R" for each substituent independently represents a linear or branched $C_{1-6}$—alkyl group; or a trimethylsilyl group;

optionally in a form of one of the stereoisomers, enantiomers, or diastereomers, a racemate, or a mixture of at least two of the stereoisomers, or a corresponding salt thereof.

4. The method according to claim 1, characterized in that $R^1$ represents a benzyl group in which the methylene moiety of the benzyl group and the aromatic moiety of the benzyl group are independently unsubstituted or substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, NHR', and NR'R", wherein R' and R" for each substituent independently represents a linear or branched $C_{1-6}$—alkyl group, and wherein the aromatic moiety is condensed with or is not condensed with a substituted or unsubstituted mono- or polycyclic ring system; or a benzhydryl group which is unsubstituted or substituted by one or more substituents independently selected from the group consisting of a $C_{1-4}$ alkyl group, a linear or branched $C_{1-6}$ alkoxy group, F, Cl, I, Br, $CF_3$, $CH_2F$, $CHF_2$, CN, OH and SH;

wherein the bond between Y and Z is saturated (Y—Z), with Y representing $CH_2$;

and Z representing CH—$R^6$;

R6 represents a phenyl group which is unsubstituted or substituted by one or more substituents independently selected from the group consisting of a $c_{1-4}$ alkyl group, an unsubstituted or substituted phenyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, N(C=O)—OR', NHR', and NR'R", wherein R' and R" for each substituent independently represents a linear or branched $C_{1-6}$—alkyl group; or a trimethylsilyl group;

optionally in a form of one of the stereoisomers, enantiomers, or diastereomers, a racemate, or a mixture of at least two of the stereoisomers, or a corresponding salt thereof.

5. The method according to claim 1, wherein the compounds are selected from the group consisting of:

[1] 2-benzyl-5-phenyl-(3a,6a-cis)-1,2,3,3a-tetrahydrocyclopenta[c]pyrrol-4(6aH)-one,

[2] 5-phenyl-2-((S)-1phenylethyl)-(3a,6a-cis)-1,2,3,3a-tetrahydrocyclopenta[c]pyrrol-4(6aH)-one,

[3] 2-(4-methoxybenzyl)-5-phenyl-(3a,6a-cis)-1,2,3,3a-tetrahydrocyclopenta[c]pyrrol-4(6aH)-one,
[4] 2-benzyl-5-(4-fluorophenyl)-(3a,6a-cis)-1,2,3,3a-tetrahydrocyclopenta[c]pyrrol-4(6aH)-one,
[5] 2-benzyl-5-(4-ethylphenyl)-(3a,6a-cis)-1,2,3,3a-tetrahydrocyclopenta[c]pyrrol-4(6aH)-one,
[6] 2-benzyl-5-(2-chlorophenyl)-(3a,6a-cis)-1,2,3,3a-tetrahydrocyclopenta[c]pyrrol-4(6aH)-one,
[7] 2-benzyl-5-(4-chlorophenyl)-(3a,6a-cis)-1,2,3,3a-tetrahydrocyclopenta[c]pyrrol-4(6aH)-one,
[8] 2-benzyl-5-(3-chlorrophenyl)-(3a,6a-cis)-1,2,3,3a-tetrahydrocyclopenta[c]pyrrol-4(6aH)-one
[9] 2-benzyl-5-(4-methoxyphenyl)-(3a,6a-cis)-1,2,3,3a-tetrahydrocyclopenta[c]pyrrol-4(6aH]-one,
[10] 2-benzyl-5-(biphenyl-4-yl)-(3a,6a-cis)-1,2,3,3a-tetrahydrocyclopenta[c]pyrrol-4(6aH)-one,
[11] 2-benzyl-5-(4-tert-butylcarbamatephenyl)-(3a,6a-cis)-1,2,3,3a-tetrahydrocyclopenta[c]pyrrol-4(6aH)-one,
[12] 2-benzyl-5-butyl-(3a, 6a-cis)-1,2,3,3a-tetrahydrocyclopenta[c]pyrrol-4(6aH]-one,
[13] 2-benzhydryl-5-phenyl-(3a,6a-cis)-1,2,3,3a-tetrahydrocyclopenta[c]pyrrol-4(6aH)-one,
[14] 2,5-dibenzyl-(3a,6a-cis)-1,2,3,3a-tetrahydrocyclopenta[c]pyrrol4(6aH)-one,
[15] 2-(4-fluorobenzyl)-5-phenyl-(3a,6a-cis)-1,2,3,3a-tetrahydrocyclopenta[c]pyrrol-4(6aH)-one,
[16] 2-benzyl-5-(trimethylsilyl)-(3a,6a-cis)-1,2,3,3a-tetrahydrocyclopenta[c]pyrrol-4(6aH)-one;
[17] 2-benzyl-(3, 6a-cis)-1,2,3,3a-tetrahydrocyclopenta[c]pyrrol-4(6aH)-one;
[18] 2-benzyl-5-tert-butyl-(3a,6a-cis)-1,2,3,3a-tetrahydrocyclopenta[c]pyrrol-4(6aH)-one,
[19] 2-benzyl-5-phenyl-(3a,6a-cis)-1,2,3,3a-hexahydrocyclopenta[c]pyrrol-4(5H)-one;
[20] ((R,S)-5,6)-2-benzyl-6-methyl-5-phenyl-(3a,6a-cis)-1,2,3,3a-tetrahydrocyclopenta[c]pyrrol-4(1H,2H,5H)-one,
[21] ((R,S)-5,6)-2-benzyl-6-butyl-5phenyl-(3a,6a-cis)-1,2,3,3a-hexahydrocyclopenta[c]pyrrol-4(1H,2H,5H)-one,
[22] ((R,S)-5,6)-2-benzyl-6-ethyl-5-phenyl-(3a,6a-cis)-1,2,3,3a-hexahydrocyclopenta[c]pyrrol-4(5H)-one;
[23] ((R,S)-5,6)-2-benzyl-6-isopropyl-5-phenyl-(3a,5a-cis)-1,2,3,3a-hexahydrocyclopenta[c]pyrrol-4(5H)-one;
[24] ((R,S)-5,6)-2-benzle-5-phenyl-6-propyl-(3a,6a-cis)-1,2,3,3a-hexahydrocyclopenta[c]pyrrol-4(5H)-one;
[25] ((R,S)-5,6)-2-benzyl-6ethyl-5-(4-fluorophenyl)-(3a,6a-cis)-1,2,3,3a-hexahydrocyclopenta[c]pyrrol-4(5H)-one;
[26] ((R,S)-5,6)-2-benzyl-5-(4-fluorophenyl)-6-propyl-(3a,6a-cis)-1,2,3,3a-hexahydrocyclopenta[c]pyrrol-4(5H)-one;
[27] ((R,S)-5,6)-2benzyl-6-butyl-5-(4-fluorophenyl)-3a,6a-cis)-1,2,3,3a-hexahydrocyclopenta[c]pyrrol-4(5H)-one;
[28] ((R,S)-5,6)-2-benzyl-5-(4-fluorophenyl)-6-methyl-(3a,6a-cis)-1,2,3,3a-hexahydrocyclopenta[c]pyrrol-4(5H)-one;
[29] ((R,S)-5,6)-2-benzyl-5,6-dibutyl-(3a,6a-cis)-1,2,3,3a-hexahydrocyclopenta[c]pyrrol-4(5H)-one;
[30] ((R,S)-5,6)-2-benzyl-5-butyl-6-ethyl-(3a,6a-cis)-1,2,3,3a-hexahydrocyclopenta[c]pyrrol-4(5H)-one;
[31] ((R,S)-5,6)-2-benzyl-5-butyl-6-methyl-(3a,6a-cis)-1,2,3,3a-hexahydrocyclopenta[c]pyrrol-4(5H)-one;
[32] ((R,S)-5,6)-2-benzyl-5-butyl-6-phenyl-(3a,6a-cis)-1,2,3,3a-hexahydrocyclopenta[c]pyrrol-4(5H)-one;
[33] ((R,S)-5,6)-2-benzyl-5-(4-chlorophenyl)-6-methyl-(3a,6a-cis)-1,2,3,3a-hexahydrocyclopenta[c]pyrrol-4(5H)-one;
[34] ((R,S)-5,6-2-benzyl-5-(4-fluorophenyl)-6-phenyl-(3a,6a-cis)-1,2,3,3a-hexahydrocyclopenta[c]pyrrol-4(5H)-one;
[35] ((R,S)-5,6)-2-benzyl-5,6-diphenyl-(3a,6a-cis)-1,2,3,3a-hxahydrocyclopenta[c]pyrrol-4(5H)-one;
[36] ((R,S)-5,6)-2-benzyl-6-(3,5-dimethylphenyl)-5-phenyl-(3a,6a-cis)-1,2,3,3a-hexahydrocyclopenta[c]pyrrol-4(5H)-one;
[37] ((R,S)-5,6)-2-benzyl-6-(4-methoxyphenyl)-5-phenyl-(3a,6a-cis)-1,2,3,3a-hexahydrocyclopenta[c]pyrrol-4(5H)-one; or
[38] ((R,S)-5,6)-2-benzyl-5-(4-chlorophenyl)-6-phenyl-(3a,6a-cis)-1,2,3,3a-hexahydrocyclopenta[c]pyrrol-4(5H)-one;

optionally in a form of one of the stereoisomers, enantiomers, or diastereomers, a racemate, or a mixture of at least two of the stereoisomers, or a corresponding salt thereof.

6. The method according to claim 1, characterized in that the pain disorder is selected from the group consisting of neuropathic pain, inflammatory pain or other pain conditions involving allodynia and/or hyperalgesia.

7. Process for the manufacture of a medicament, said process comprising including in said medicament a compound of formula (I) as defined in claim 1.

\* \* \* \* \*